United States Patent [19]
Bardy et al.

[11] Patent Number: 5,257,621
[45] Date of Patent: Nov. 2, 1993

[54] APPARATUS FOR DETECTION OF AND DISCRIMINATION BETWEEN TACHYCARDIA AND FIBRILLATION AND FOR TREATMENT OF BOTH

[75] Inventors: Gust H. Bardy, Seattle, Wash.; Walter H. Olson, North Oaks, Minn.; David K. Peterson, Mounds View, Minn.; Robert T. Taepke, Fridley, Minn.

[73] Assignee: Medtronic, Inc., Minneapolis, Minn.

[21] Appl. No.: 10,926

[22] Filed: Jan. 29, 1993

Related U.S. Application Data

[63] Continuation of Ser. No. 750,679, Aug. 27, 1991, Pat. No. 5,193,535.

[51] Int. Cl.$^5$ ............................................. A61N 1/39
[52] U.S. Cl. ...................................... 607/5; 128/705; 607/4
[58] Field of Search ............. 128/419 PG, 419 D, 705

[56] References Cited

U.S. PATENT DOCUMENTS

| | | |
|---|---|---|
| Re.27,757 | 3/1987 | Mirowski . |
| 3,737,579 | 6/1973 | Bolduc . |
| 3,937,266 | 2/1976 | Cordone et al. . |
| 4,088,140 | 5/1978 | Rockland et al. . |
| 4,354,497 | 10/1982 | Kahn . |
| 4,375,817 | 3/1983 | Engle et al. . |
| 4,384,585 | 5/1983 | Zipes . |
| 4,502,276 | 3/1985 | Markowitz et al. . |
| 4,523,595 | 6/1985 | Zibell . |
| 4,548,209 | 10/1985 | Wielders . |
| 4,577,633 | 3/1986 | Berkovits et al. . |
| 4,577,634 | 3/1986 | Gessman . |
| 4,587,970 | 5/1986 | Holley et al. . |
| 4,712,554 | 12/1987 | Garson, Jr. . |
| 4,726,380 | 2/1988 | Vollmann et al. . |
| 4,754,753 | 7/1988 | King . |
| 4,790,317 | 12/1988 | Davies . |
| 4,799,493 | 1/1989 | DuFault . |
| 4,800,883 | 1/1989 | Winstrom . |
| 4,817,634 | 4/1989 | Holleman et al. . |
| 4,819,643 | 4/1989 | Menken . |
| 4,830,006 | 5/1989 | Halusha et al. . |
| 4,880,005 | 11/1989 | Pless et al. . |
| 4,949,719 | 8/1990 | Pless et al. . |
| 4,949,730 | 8/1990 | Cobben et al. . |
| 4,953,551 | 9/1990 | Mehra et al. . |
| 5,193,535 | 3/1993 | Bardy et al. .................... 128/419 D |

OTHER PUBLICATIONS

Experimental Ventricular Defibrillation with an Automatic and Completely Implanted System, Schuder et al., Transactions American Society for Artificial Internal Organs, 16:207, 1970.

Automatic Implantable Cardioverter Defibrillator Structural Characteristics Pace Maganzine, vol. 7, Nov.-Dec. 1984 Part II pp. 1331-1334 by Mower et al.

Automatic Tachycardia Recognition, by R. Arzbaecher et al. Pace, May-Jun., 1984 pp. 541-547.

Measurements of Differences in Timing and Sequence Between Two Entricular Electrodes as a Means of Tachycardia Differentiation by Mercando et al. Pace, vol. 9, pp. 1069-1078, Nov.-Dec., 1986 Part II.

Reliable-Wave Detection from Ambulatory Subjects by Thakor et al. Biomedical Science Instrumentation, vol. 4, pp. 67-72, 1978.

*Primary Examiner*—William E. Kamm
*Attorney, Agent, or Firm*—Reed A. Duthler; Harold R. Patton

[57] ABSTRACT

An implantable cardioverter/defibrillator provided with method and apparatus for discrimination between ventricular tachycardia and ventricular fibrillation. The device is provided with two pairs of electrodes, each pair of electrodes coupled to processing circuitry for identifying a predetermined fiducal point in the electrical signal associated with a ventricular depolarization. The cumulative beat to beat variability of the intervals separating the two identified fiducal points, over a series of detected depolarizations is analyzed. The result of this analysis is used to distinguish between ventricular tachycardia and ventricular fibrillation.

8 Claims, 12 Drawing Sheets

APPARATUS FOR DETECTION OF AND DISCRIMINATION BETWEEN TACHYCARDIA AND FIBRILLATION AND FOR TREATMENT OF BOTH

This is a continuation of copending application Ser. No. 07/750,679 filed on Aug. 27, 1991 now U.S. Pat. No. 5,193,535.

BACKGROUND OF THE INVENTION

This invention relates to implantable stimulators generally and more particularly to implantable cardioverters and defibrillators.

Early automatic tachycardia detection systems for automatic implantable cardioverter/defibrillators relied upon the presence or absence of electrical and mechanical heart activity (such as intramyocardial pressure, blood pressure, impedance, stroke volume or heart movement) and or the rate of the electrocardiogram to detect hemodynamically compromising ventricular tachycardia or fibrillation. For example, the 1961 publication by Dr. Fred Zacouto, Paris, France, entitled, "Traitement D'Urgence des Differents Types de Syncopes Cardiaques du Syndrome de Morgangni-Adams-Stokes" (National Library of Medicine, Bethesda, Md.) describes an automatic pacemaker and defibrillator responsive to the presence or absence of the patient's blood pressure in conjunction with the rate of the patient's electrocardiogram to diagnose and automatically treat brady and tachyarrhythmias.

Later detection algorithms proposed by Satinsky, "Heart Monitor Automatically Activates Defibrillator", Medical Tribune, 9, No. 91:3, Nov. 11, 1968, and Shuder et al "Experimental Ventricular Defibrillation with an Automatic and Completely Implanted System", Transactions American Society for Artificial Internal Organs, 16:207, 1970, automatically detected and triggered defibrillation when the amplitude of the R-wave of the electrocardiogram fell below a predetermined threshold over a predetermined period of time. The initial system proposed by Mirowski et al in U.S. Pat. No. Re 27,757, which similarly relied upon the decrease in the amplitude of a pulsatile right ventricular pressure signal below a threshold over a predetermined period of time, was abandoned by Mirowski et al in favor of the rate and/or probability density function morphology discrimination as described in Mower et al, "Automatic Implantable Cardioverter-Defibrillator Structural Characteristics", PACE, Vol. 7, November-December 1984, Part II, pp. 1331-1334.

More recently, others have suggested the use of high rate plus acceleration of rate or "onset" (U.S. Pat. No. 4,384,585) with sustained high rate and rate stability (U.S. Pat. No. 4,523,595). As stated in the article "Automatic Tachycardia Recognition", by R. Arzbaecher et al, PACE, May-June 1984, pp. 541-547, antitachycardia pacemakers that were undergoing clinical studies prior to the publication of that article detected tachycardia by sensing a high rate in the chamber to be paced. The specific criteria to be met before attempting tachyarrhythmia termination by pacing involved a comparison of the detected heart rate to a preset threshold, such as 150 beats per minute (400 millisecond cycle length) for a preselected number of beats. As stated above, other researchers had suggested the rate of change of rate or suddenness of onset, rate stability and sustained high rate as additional criteria to distinguish among various types of tachyarrhythmias.

Very generally, the systems that depend upon the aforementioned rate criteria are capable of discriminating tachycardia in greater or lesser degree from normal heart rate but can have difficulty discriminating high rate ventricular tachycardias from ventricular fibrillation. In practical applications, a common approach has been to specify discrete rate zones for ventricular fibrillation and ventricular tachycardia, each defined by minimum rates or minimum R-R intervals. However, in some patients, ventricular tachycardia and ventricular fibrillation may have similar rates that make it difficult to distinguish ventricular fibrillation from high rate ventricular tachycardia and supraventricular tachycardias.

Ventricular fibrillation is characterized by chaotic electrical activity which presents highly variable depolarization wavefronts which are propagated in directions which differ from those seen during normal sinus rhythm. Ventricular tachycardias may result from reentry conduction through diseased tissue, which results in depolarization wavefronts, also typically propagated in directions which differ from those seen during normal sinus rhythm. Detection of the occurrence of depolarization wavefronts having directions of propagation which differ from those seen in normal sinus rhythm has been used in various ways in devices intended to detect the presence of ventricular tachycardia or fibrillation.

For example, U.S. Pat. Nos. 3,937,266, 4,088,140 and 4,354,497 describe systems intended to distinguish abnormal ventricular depolarization wavefronts from depolarization wavefronts which originate in the HIS bundle purkinje fiber system. These devices employ a multitude of spaced electrodes coupled to sense amplifiers and attempt to use the relative arrival times of the wavefronts at the various electrodes to detect the occurrence of abnormal conduction.

U.S. Pat. No. 4,754,753 presents a method and apparatus for sensing the probable onset of ventricular fibrillation or pathologic tachyarrhythmias by observing the direction of the depolarization wavefront to predict the onset of harmful ventricular tachyarrhythmias. Detection is accomplished through the use of a multitude of spatially oriented electrodes situated on a pacing lead to provide a vector representation of the direction of propagation of depolarization wavefronts.

Others, such as the inventors of U.S. Pat. No. 4,712,554, have proposed distinguishing between sinus and nonsinus atrial depolarizations by determining the sequence of atrial activation through the use of bipolar or quadrapolar electrodes placed high in the right atrium. U.S. Pat. No. 4,577,634 employs quadrapolar atrial and ventricular electrodes for distinguishing retrograde P-wave conduction from normal sinus propagation to avoid pacemaker mediated tachycardia. In a further U.S. Pat. No. 4,790,317, it is proposed to recognize ventricular tachycardia and ventricular fibrillation by comparison of pulse sequences which are obtained when sensing from at least one position on each ventricular epicardial surface. A change in the sequence of activations and in the timing of signals sensed at the two sensor positions is detected and used to indicate either ventricular tachycardia or ventricular fibrillation.

It has also been proposed in the article entitled "Measurement of Difference in Timing and Sequence Between Two Ventricular Electrodes as a Means of Tachycardia Differentiation", by Mercando et al, appearing in PACE, Vol. 9, pp. 1069-1078, November-December, 1986, Part II, that the use of two ventricular sensing electrodes to determine electrical activation sequence in the expectation that the sequence could provide a method for differentiation of normal from abnormal rhythms by implantable antitachycardia devices. Simultaneous recordings from two ventricular sites were obtained during implantation of several devices or programmed electrical stimulation studies. Recordings were made of normal sinus rhythm, ventricular tachycardia, and during premature ventricular contractions. The time intervals between the intrinsic deflections of the two electrograms derived from the ventricular electrodes were measured in a number of the patients and the mean and range values were derived. The authors concluded that the measured mean values of the time intervals over a series of beats could be employed in individual patients to differentiate between normal and abnormal complexes. However, while the authors concluded that it would be feasible to detect differences in sequence timing using two ventricular electrodes in order to distinguish normal sinus beats from ectopic beats, the disclosed range of mean time intervals shows considerable overlap.

Yet another proposal for distinguishing between various types of tachyarrhythmia and ventricular fibrillation is disclosed in U.S. Pat. No. 4,799,493 issued to DuFault. In the device disclosed in this patent, the Widrow-Hoff algorithm is utilized for estimation of a transfer function as a means of discriminating between tachyarrhythmias. The transfer function, once determined generates a replica (estimate) of the signal from a first electrode pair, based on the signal from a second electrode pair. The signal from the first electrode pair can be subtracted from the derived replica (estimate) signal to produce a null signal, in the presence of stable rhythm. Filters specifically tuned to produce null signals in the presence of sinus tachycardia or ventricular tachycardia are disclosed, as well as adaptive filters which automatically converge in the presence of stable rhythm. The automatically adapting filters are disclosed as capable of distinguishing between ventricular fibrillation and tachycardias, in that the LMS algorithms will not allow convergence in the presence of fibrillation. This technique is also described in the article "Dual Lead Fibrillation Detection for Implantable Defibrillators Via LMS Algorithm" by DuFault et al., published in *Computers and Cardiology* 1986, IEEE Computer Society Press, pp. 163-166.

SUMMARY OF THE INVENTION

In the context of an automatic implantable device for treating bradyarrhythmias, tachyarrhythmias and fibrillation, the present invention comprises a method and apparatus for reliable discrimination of ventricular fibrillation from high rate monomorphic ventricular tachycardias. The ventricular tachycardia/ventricular fibrillation discriminator of the present invention preferably employs two electrode pairs. Each electrode pair is coupled to detection circuitry for identifying the R points in time at which the sensed electrical signals resulting from the passage of a depolarization wavefront meet certain predetermined criteria, hereafter referred to as the first and second "fiducial points". The cumulative variability of the time intervals separating the occurrence of the first and second fiducial points over a series of beats is used to distinguish fibrillation from high rate ventricular tachycardia.

The electrode pairs may include a common electrode between the two pairs, or may comprise four separate electrodes. The criteria for identifying the first and second fiducial points may be the same or may differ. Identification of the time of occurrence of a first defined fiducial point in the sensed signal from one of the electrode pairs may be used to define a time window during which the device attempts to identify a second fiducial point in the sensed signal from the other electrode pair. The time interval δ separating the two fiducial points associated with a single detected depolarization wavefront is measured and stored. The cumulative variability of the value of δ over a series of detected depolarization wavefronts in conjunction with detection of a high ventricular rate is used to distinguish ventricular fibrillation from high rate tachycardia.

The tachycardia/fibrillation discriminator is intended to be used in conjunction with an implantable pacemaker/cardioverter/defibrillator which provides differing therapies for detected ventricular tachycardias and detected ventricular fibrillation. For example, in response to detection of a tachycardia, the device may provide burst pacing, overdrive pacing or some other antitachycardia pacing regimen. Alternatively, it may provide a low to high energy cardioversion pulse. Typically, in response to detection of fibrillation, the device will provide a defibrillation pulse at an amplitude significantly higher than a cardioversion pulse.

It is believed that the invention is optimally embodied in a device which is capable of differentiating between low rate tachycardia, high rate tachycardia and fibrillation, and which provides three increasingly aggressive therapy sets for these three classes of arrhythmias. Detection of low rate tachycardias may be accomplished using any of the numerous detection methodologies known to the art, as applied to detected heart rates exceeding a lower tachycardia detection rate. The tachycardia/fibrillation discriminator of the present invention in such a device will typically be dependant on detection of a heart rate substantially in excess of the lower tachycardia detection rate. In such devices, the discriminator will serve primarily to distinguish between high rate tachycardia and fibrillation.

The method and apparatus of the present invention may be conveniently realized by providing a first pair of endocardial, myocardial or epicardial electrodes spaced apart from one another in or on the ventricles of the heart and a second pair of electrodes which may, for example, include one of the electrodes of the first pair and a large surface defibrillation electrode or a remote, indifferent electrode such as the metal housing of the implantable cardioverter/defibrillator. Alternatively, the second electrode pair might be two large surface defibrillation electrodes. Sense amplifiers are provided for each electrode pair.

A ventricular electrode pair may be used for detecting the near field, bipolar electrogram and the first fiducial point defined by the circuitry associated with this electrode pair may correspond to traditional R-wave detection criteria known to the art. The output signals from the R-wave detector define the time of occurrence of the first fiducial point and also may be used for measuring the duration of the intervals separating ventricular depolarizations (R-R intervals) to determine whether the heart rate is sufficiently rapid to activate the tachycardia/fibrillation discrimination function.

In the event that the detected heart rate is sufficiently rapid, the signals from the second electrode pair may be analyzed by the detection circuitry associated therewith to identify the time of occurrence of the second fiducial point. The time interval $\delta_i$ separating the two fiducal points associated with an individual depolarization wavefront is then be determined. The beat to beat variation ($\delta_i - \delta_{i-1}$) of the measured intervals $\delta$ separating the first and second fiducial points is measured and the cumulative variability of the values of $\delta$ over a series of detected depolarization wavefronts is compared to a cumulative variability threshold to detect fibrillation.

The measurement of cumulative variability may be accomplished by summation of the beat to beat differences ($\delta_i - \delta_{i-1}$), with detection of fibrillation occurring when the sum exceeds a cumulative variability threshold. The calculated individual values of ($\delta_i - \delta_{i-1}$) may instead be compared to a threshold value and the number of values exceeding the threshold may be counted, with detection of fibrillation occurring when the count exceeds a cumulative variability threshold. Other measures of cumulative variability may also be employed.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENTS

Figure 1:
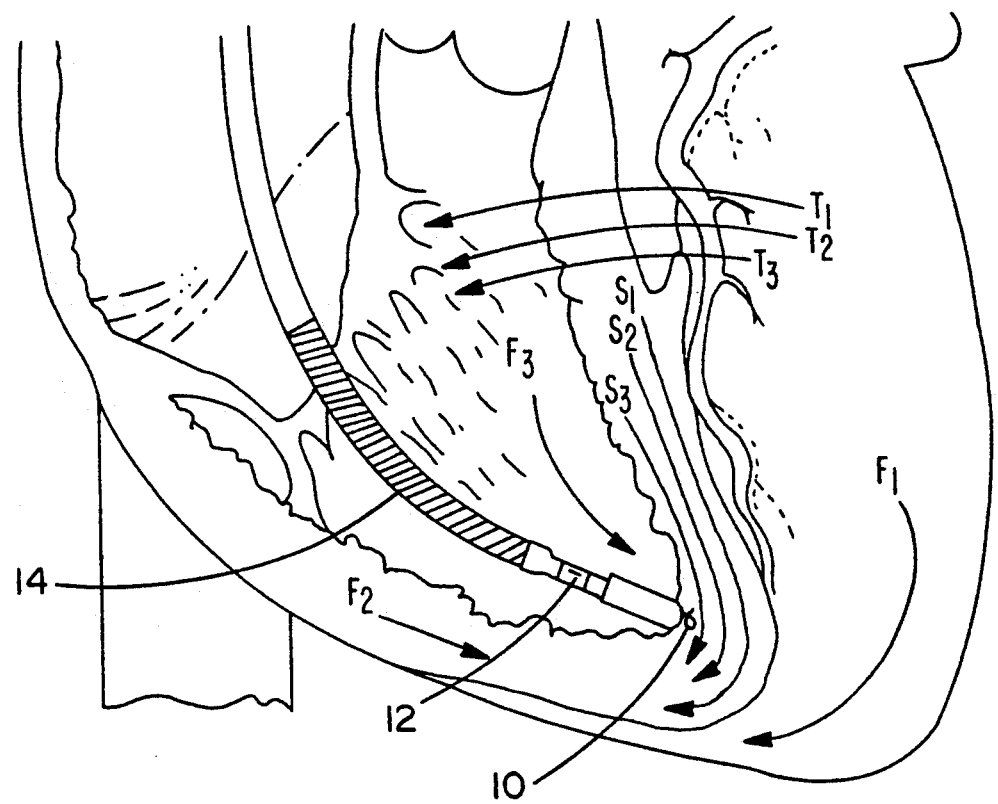
FIG. 1 is a representation of the heart, and an implanted electrode lead, illustrating the theory underlying the present invention.

FIG. 1 is a cutaway view of the heart, illustrating a ventricular defibrillation lead carrying a bipolar electrode pair located at the right ventricular apex. The bipolar electrode pair includes a tip electrode 10, which takes the form of a helical electrode screwed into the right ventricular myocardium and a ring electrode 12. The lead also includes an elongated coiled defibrillation electrode 14. The illustrated lead corresponds generally to the leads described in allowed U.S. patent application Ser. No. 07/284,955 by Bardy for an Endocardial Defibrillation Electrode system, but other defibrillation leads may also be employed.

In conjunction with FIG. 1, it should be understood that one of the two electrode pairs used to sense the first and second fiducial points discussed above may include ring electrode 12 and tip electrode 10. The other electrode pair may include ring electrode 12 and a second electrode, typically one of the defibrillation electrodes included in the lead system implanted with the pacemaker/cardioverter/defibrillator.

The general path of propagation of three successive depolarization wavefronts associated with a sinus rhythm is illustrated by the arrows labeled "S1, S2, S3". The wavefronts proceed down the septum of the heart, and then expand outward and upward around the right and left ventricles. This pathway of propagation also is present in the case of a supraventricular tachycardia such as a nodal tachycardia or a sinus tachycardia, and is consistent from beat to beat.

An example of the general path of propagation of three successive depolarization wavefronts associated with a monomorphic ventricular tachycardia is illustrated by the arrows labeled "T1, T2, T3". In the case of monomorphic ventricular tachycardia, the direction of propagation, with respect to any particular electrode pair may be the same or different from that of normal sinus rhythm. However, the direction of propagation will be approximately the same from beat to beat.

Also illustrated are examples of the directions of propagation of three successive depolarization wavefronts associated with ventricular fibrillation, illustrated by the arrows labeled "F1, F2, F3". The hallmark of ventricular fibrillation is the chaotic variation in the spread of the activation wavefront from depolarization to depolarization as opposed to constancy of wavefront propagation from depolarization to depolarization as seen in supra-ventricular or monomorphic ventricular tachycardia. As illustrated, the direction of wavefront propagation past electrodes 10 and 12 varies substantially from one wavefront to the next.

It is this beat to beat variability in the direction of wavefront propagation during fibrillation that allows the discriminator of the present invention to distinguish ventricular fibrillation from ventricular tachycardia, whether the tachycardia takes the form of a ventricular tachycardia, a supraventricular tachycardia, or a sinus tachycardia. In the case illustrated in FIG. 1, the first electrode pair, including electrodes 10 and 12, will sense a different electrical signal from the second electrode pair, including electrode 12 and a subcutaneous electrode or defibrillation electrode. With varying direction of waveform propagation, the relative timing of the two fiducial points derived from the electrode pairs will vary.

While the same detection criteria for the first and second fiducial points may be employed, it is believed that it may be advantageous to use differing fiducial point detection criteria for the detection circuitry associated with the two electrode pairs. The use of two differing fiducial point detection criteria is believed likely to increase the measured variability of the interval δ between the two fiducial points in the case of ventricular fibrillation without correspondingly increasing the variability of the time interval δ between the two fiducial points in the case of a ventricular tachycardia. However, use of either the same or different criteria for the two fiducal points is believed workable.

Figure 2:
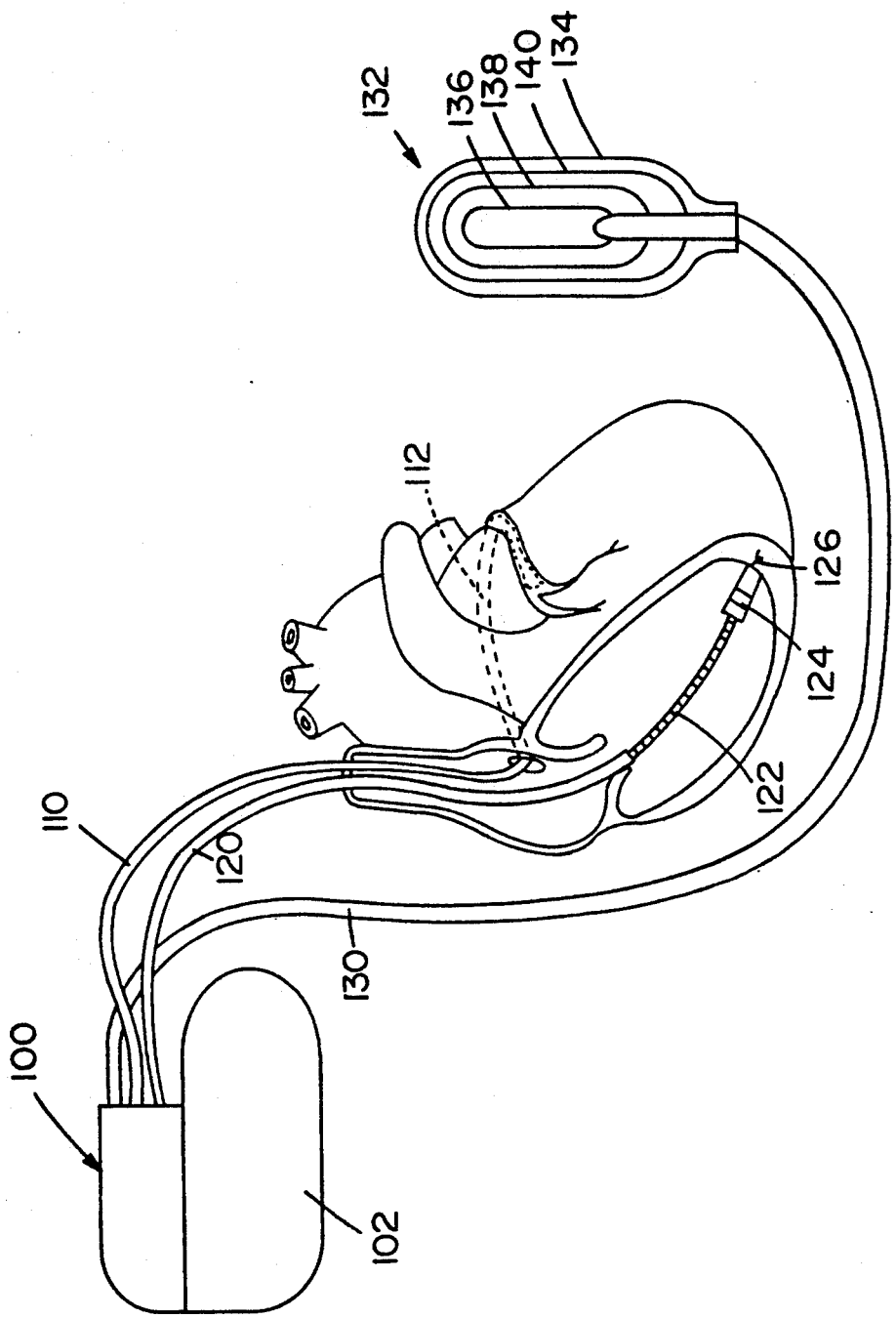
FIG. 2 illustrates a tranvenous/subcutaneous electrode system appropriate for use with a pacemaker/cardioverter/defibrillator embodying the present invention.

FIG. 2 illustrates an implantable pacemaker/cardioverter/defibrillator 100 and its associated lead system, as implanted in and adjacent to the heart. As illustrated, the lead system comprises a coronary sinus lead 110, a right ventricular lead 120, and a subcutaneous lead 130. The coronary sinus lead is provided with an elongated electrode located in the coronary sinus and great vein region at 112, extending around the heart until approximately the point at which the great vein turns downward toward the apex of the heart. The right ventricular lead 120, corresponds to the lead illustrated in FIG. 1, and includes an elongated defibrillation electrode 122, a ring electrode 124, and helical electrode 126, which is screwed into the tissue of the right ventricle at the right ventricular apex. Leads 110 and 120 may correspond to the leads disclosed in allowed U.S. patent Ser. No. 07/284,955 by Bardy for an "Endocardial Defibrillation Electrode System", filed Dec. 15, 1988 and incorporated herein by reference in its entirety. A subcutaneous lead 130 is also illustrated, implanted subcutaneously in the left chest. Lead 130 includes a large surface electrode pad 132, carrying elongated electrode coils 136, 138 and 140. Electrode 132 may correspond to the electrode illustrated in allowed U.S. patent application Ser. No. 07/376,730, by Lindemans et al. for a Medical Electrical Lead, filed Jul. 7, 1989 and incorporated herein by reference in its entirety.

In conjunction with the present invention, the lead system illustrated provides numerous electrode pairs which may be employed to practice the invention. For example, the first electrode pair may comprise ring electrode 124 and tip electrode 126, with the second electrode pair comprising ring electrode 124 and subcutaneous defibrillation electrode 132. Alternatively, the second pair of electrodes could comprise defibrillation electrode 112 in conjunction with the subcutaneous electrode 132, or in conjunction with defibrillation electrode 122.

The second electrode pair may instead comprise small surface area electrodes (not illustrated) provided on the lead bodies of the coronary sinus lead 110 and/or the ventricular lead 120. For example, an additional electrode or electrode pair could be mounted to the coronary sinus lead or to the ventricular lead such that the electrode or electrode pair would be located high in the ventricle or in the superior vena cava when implanted.

Figure 3:
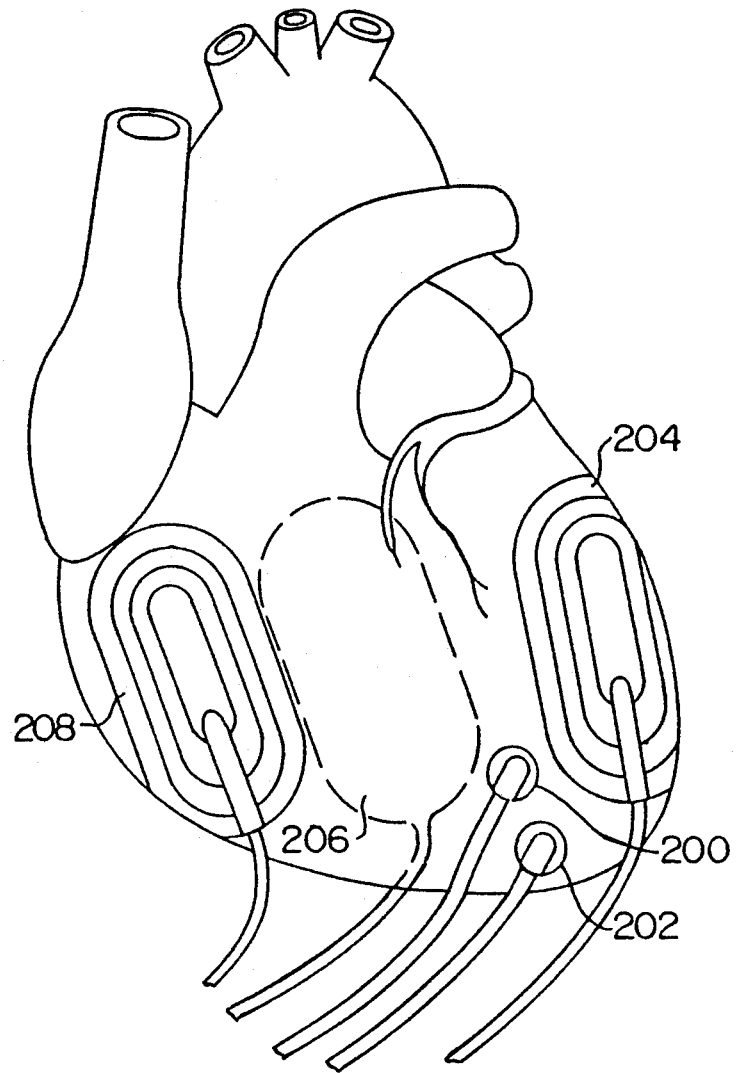
FIG. 3 illustrates a myocardial/epicardial electrode system appropriate for use with a pacemaker/cardioverter/defibrillator embodying the present invention.

FIG. 3 illustrates an epicardial and myocardial electrode system for use in conjunction with an implantable pacemaker/cardioverter/defibrillator. In this case, two unipolar myocardial electrodes 200 and 202 are located on the left ventricle of the heart. These electrodes may correspond to those illustrated in U.S. Pat. No. 3,737,579, issued to Bolduc on Jun. 5, 1973, and incorporated herein by reference in its entirety. Also illustrated are three large surface electrodes 204, 206 and 208, spaced around the ventricles of the heart. These electrodes may correspond to the electrodes disclosed in U.S. Pat. No. 4,817,634, issued to Holleman et al. on Apr. 4, 1989, also incorporated herein by reference in its entirety.

In the context of the present invention, electrodes 200 and 202 may constitute the first electrode pair and the second electrode pair may include either of electrodes 200 and 202 in conjunction with one of the large surface defibrillation electrodes 204, 206, 208 or may comprise two of the defibrillation electrodes.

Alternatively, the first electrode pair might comprise electrode 200 in conjunction either with one of the large surface electrodes 204, 206, 208 or in conjunction with an electrode located on the housing of the implantable device and the second electrode pair might comprise electrode 202, also paired with one of the large surface area electrodes 204, 206, 208 or with a remote indifferent electrode located on the housing of the implantable pacemaker/cardioverter/defibrillator.

As a practical matter, in the systems as illustrated in FIGS. 2 and 3, a pair of small surface area electrodes corresponding generally to electrodes 124 and 126 in FIG. 2 or to electrodes 200 and 202 in FIG. 3 will generally be used for delivery of cardiac pacing pulses and for sensing the occurrence of R-waves in order to reset the timing of the cardiac pacing function and for most purposes associated with tachyarrhythmia recognition. The invention may conveniently be practiced by employing electrodes such as these, in conjunction with an R-wave detector of a known type to provide a signal indicative of the occurrence of the first fiducial point as discussed above.

Figure 4:
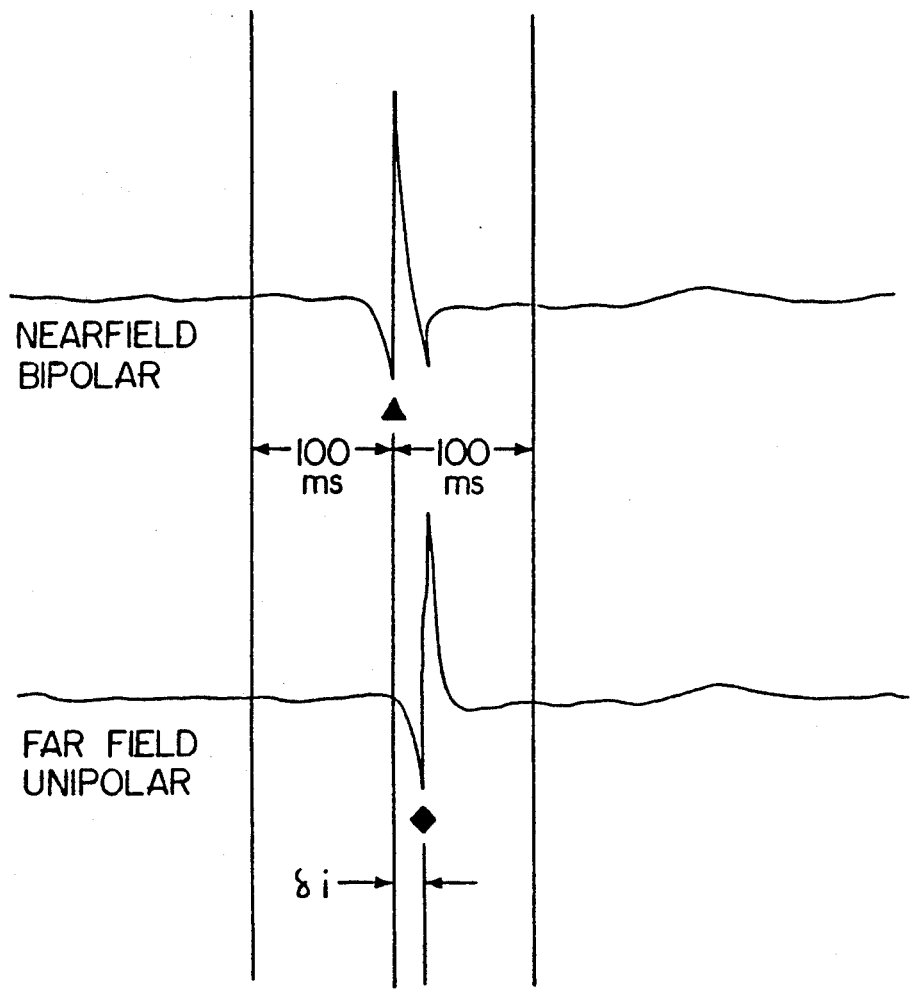
FIG. 4 is an illustration of the identification of the first and second fiducial points in sensed signals from two differing pairs of electrodes, and of the calculation of the interval $\delta$, separating the first and second fiducial points for a single depolarization.

FIG. 4 is a set of human EGM tracings illustrating the detection of the first and second fiducial points associated with a detected R-wave and the measurement of the time interval δ separating them. As illustrate, the top ECG tracing is taken between an electrode pair located in the right ventricle, comprising a tip and ring electrode generally corresponding to electrodes 124 and 126 illustrated in FIG. 2. The lower tracing is taken between the proximal one of the bipolar pair in the right ventricle, corresponding generally to electrode 124, and a remote, subcutaneous electrode.

As illustrated, the fiducial point identified by the processing circuitry coupled to the first electrode pair, in the upper tracing, corresponds to the output of an R-wave detection circuit employing a bandpass filter followed by a detector having an automatically adjusting threshold level. The occurrence of the first fiducial point, illustrated by the symbol "▲", occurs when the band pass filtered signal from the ventricular electrode pair exceeds the detection threshold.

The fiducial point defined by the processing circuitry associated with the second electrode pair is the detected point of maximum slope of the bandpass filtered signal from the second electrode pair, as illustrated by the symbol "♦". The interval δ separating the first and second fiducial points is also illustrated along with a time window extending plus or minus 100 milliseconds from the detection of the first fiducial point "▲", during which detection of the second fiducial point "♦" is attempted.

As defined in the present application, the time differential δ between the occurrence of the first and second fiducial points is determined by noting the time of occurrence of the first fiducial point and subtracting it from the measured time of occurrence of the second fiducial point. The resulting time interval δ may therefore have a positive or negative value.

Figure 5:
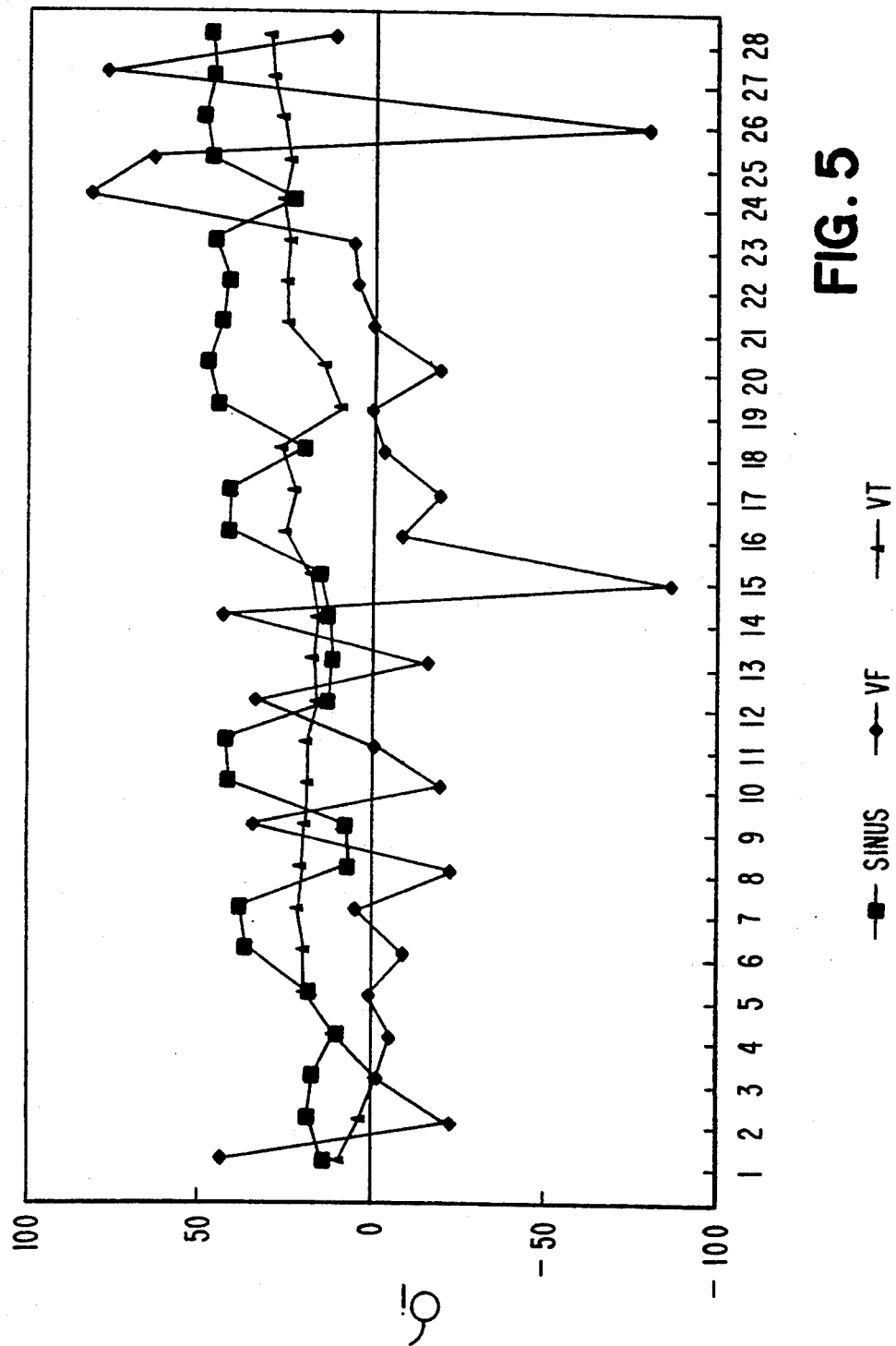
FIG. 5 is a graph illustrating the measurement of the interval $\delta$ separating the first and second fiducial points, taken over an extended series of detected R-waves or depolarizations during sinus rhythm, ventricular fibrillation, and ventricular tachycardia.

FIG. 5 shows a sequence of measured values for δ, as taken during rapid sinus rhythm, ventricular fibrillation and ventricular tachycardia at various rates. As illustrated, over a series of detected R-waves, the values of δ in the presence of confirmed ventricular fibrillation vary over a substantially greater range than during sinus or other supraventricular rhythm or during ventricular tachycardia. Testing by the inventors has shown that the relationship illustrated holds true for ventricular tachycardia and ventricular fibrillation even at similar rates (e.g. >250 bpm).

Figure 6:
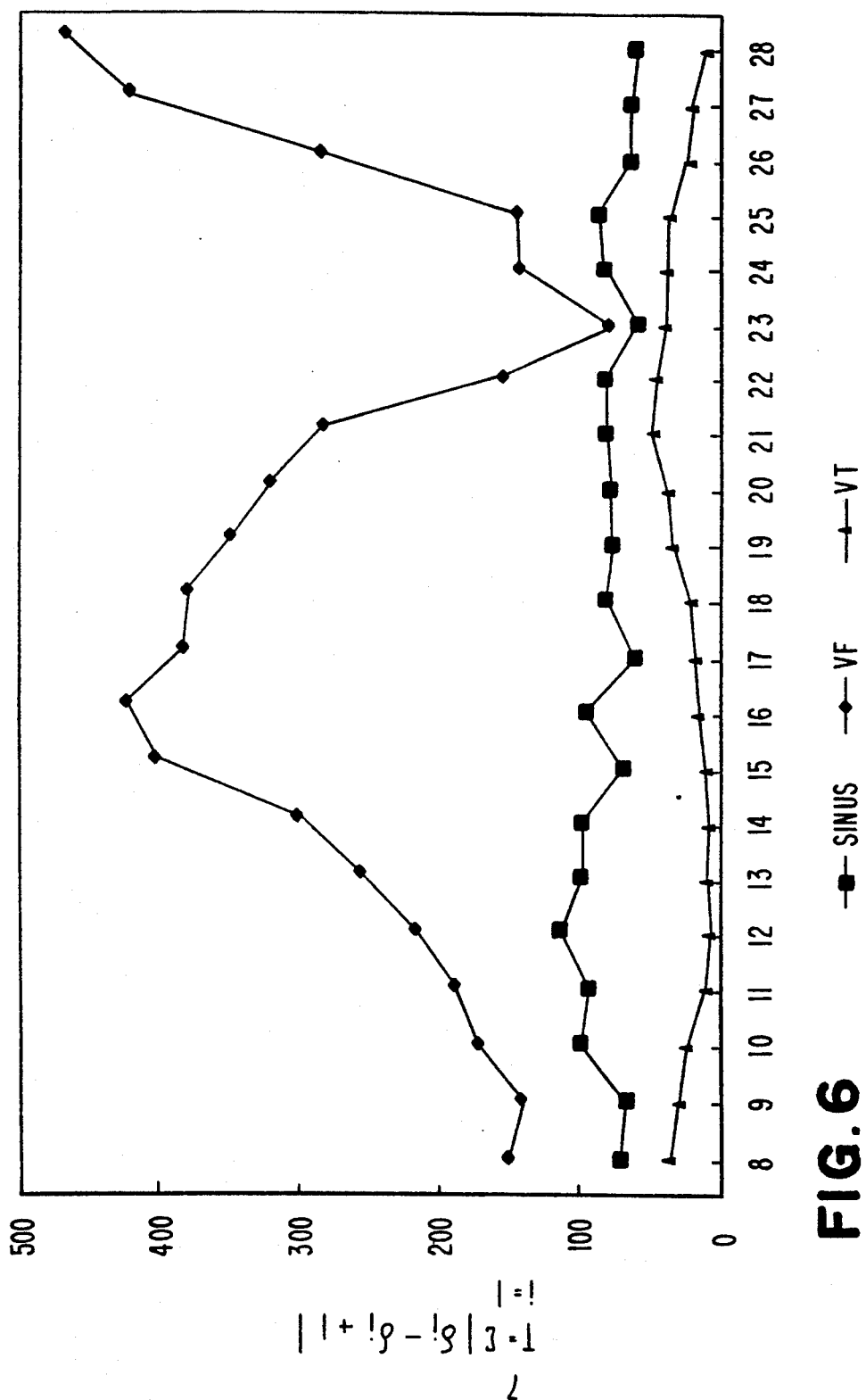
FIG. 6 is a graph illustrating the measurement of variability in the measured intervals $\delta$ separating the first and second fiducial points, as performed by the tachycardia/fibrillation discriminator of the present invention, operating over extended series of detected R-waves in each of the three rhythms illustrated in FIG. 5.

FIG. 6 illustrates the operation of the tachycardia/fibrillation discriminator on the data illustrated in FIG. 5. In FIG. 6, the regularity of the value of δ is assessed by means of determining its cumulative beat-to-beat variability over a sequence of eight preceding detected R-waves using a method hereafter referred to as the "summation" method. The chart begins with the eighth detected R-wave, representing the first point at which variability has been calculated. Each graphed point represents the cumulative variability over the preceding eight values of δ. Cumulative variability τ of the value of δ may be calculated according to the equation:

$$T = \sum_{i=1}^{7} |\delta_i - \delta_{i+1}|$$

The cumulative variability as calculated above is the sum of the absolute values of the beat to beat differences between a series of successively measured values of δ. The sum is compared to a predetermined cumulative variability threshold and if it exceeds the threshold, fibrillation is detected. For example, if the cumulative variability over eight measured values of δ exceeds 200 ms, fibrillation may be detected.

An alternative method of calculation of cumulative variability for a series of measured values of δ is hereafter referred to as the "rank ordered difference" method. For a series of L measured values of δ, each measured value of δ is compared with M previous values of δ, e.g. $(\delta_i - \delta_{i-1})$, $(\delta_i - \delta_{i-2})$, $(\delta_i - \delta_{i-3})$, if M=3. Of these calculated differences, the greatest absolute difference $(V_i)$ is selected as a measure of beat to beat variability associated with $\delta_i$. The L values of $V_i$ are compared to a predetermined threshold t, and a count C of the number of values of $V_i$ greater than the threshold is made. If more than K of L values of $V_i$ are greater than the threshold, i.e. C>K, fibrillation is detected. An exemplary set of parameters for implementation of this method of cumulative variability calculation could be L=8, M=3, t=30 ms and K=2. The inventors of the present application have found that the rank ordered difference method of cumulative variability assessment provides a high sensitivity to the occurrence of ventricular fibrillation while maintaining a high specificity for ventricular tachycardias.

Other calculations of the cumulative variability of the measured values of δ, such as the standard deviation of the measured values of δ over a series of beats, the standard error of the mean measured value of δ over a series of beats or the range of measured values of δ over a series of beats might also be used.

As illustrated in FIGS. 5 and 6, the cumulative variability over a sequence of detected depolarizations is almost always substantially higher for ventricular fibrillation than for either sinus rhythm or for ventricular tachycardia. This has been found to be true using both methods of cumulative variability calculation discussed above, but the rank ordered difference method is believed to be somewhat superior in avoiding inappropriate detection of fibrillation.

Greater separation of the detected levels of beat to beat variability associated with fibrillation and tachycardia can be accomplished by measuring the cumulative variability of the values of δ over a longer sequence of detected R-waves. However, this will come at the expense of extending the period of time the discriminator requires in order to operate. As a practical matter, it is believed the in most cases, measuring the variability of the values of δ over a sequence of eight to twelve measurements of δ will be adequate to discriminate ventricular fibrillation from ventricular tachycardia or from sinus or supraventricular tachycardias. For purposes of practical implementation, the number of measurements of δ employed by the discriminator may be made a programmable parameter, allowing the physician to optimize the operation of the discriminator to fit the specific needs of individual patients.

As implemented, the VT/VF discrimination function may be applied employing all detected depolarizations in a series of sequential R-R intervals. Alternatively, the discrimination function may employ only some of the detected depolarizations. As discussed below, the discrimination function is preferably designed such that it provides a measurement of δ only for individual depolarizations which define the endpoint of R-R intervals sufficiently short to meet the rate criteria for fast tachycardia or fibrillation detection.

Figure 7:
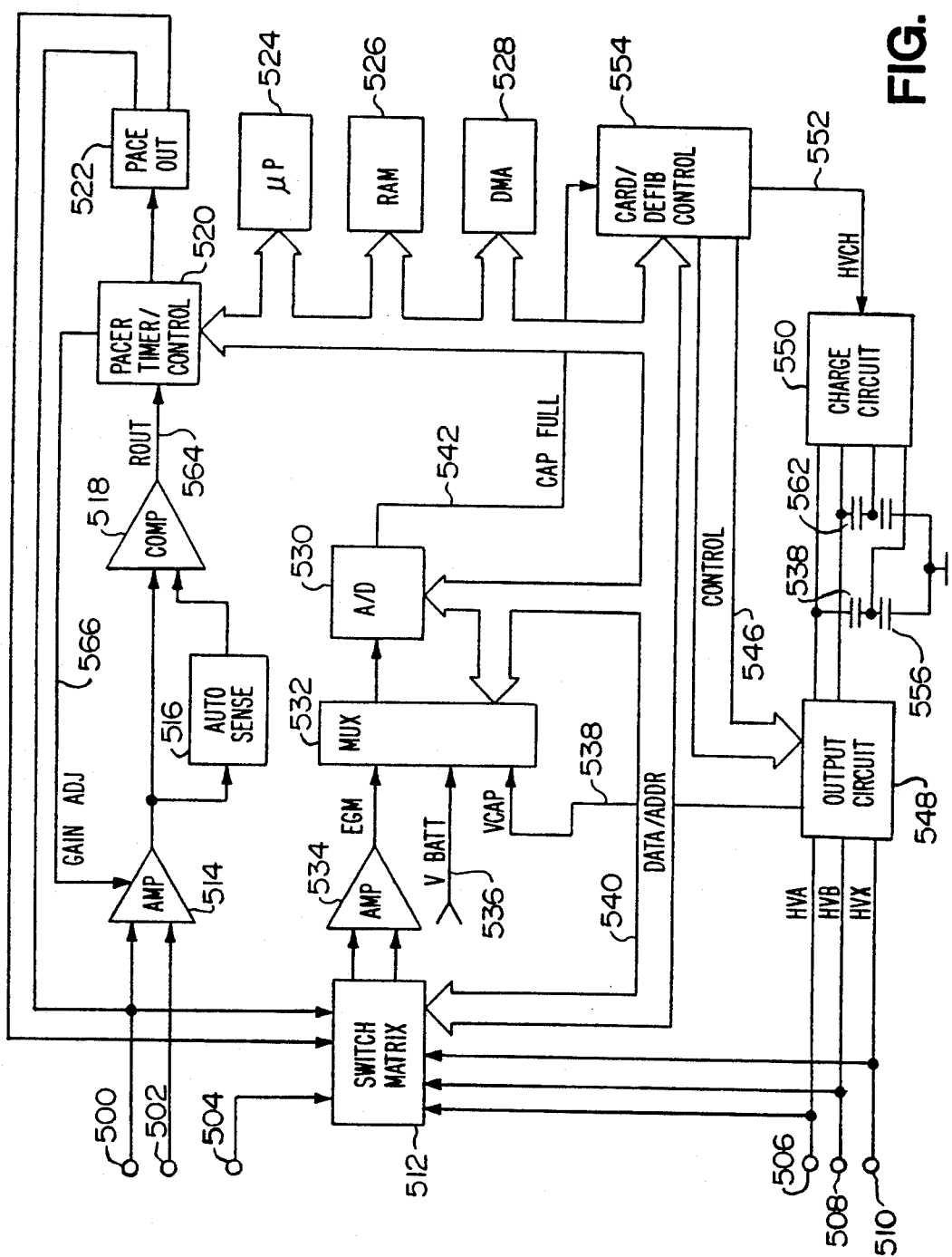
FIG. 7 is a schematic block diagram illustrating the structure of one embodiment of an implantable pacemaker/cardioverter/defibrillator in which the present invention may be embodied.

FIG. 7 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/defibrillators as disclosed in prior U.S. Pat. No. 4,548,209, issued to Wielders, et al on Oct. 22, 1985, U.S. Pat. No. 4,693,253, issued to Adams et al on Sep. 15, 1987, U.S. Pat. No. 4,830,006, issued to Haluska et al on May 6, 1989 and U.S. Pat. No. 4,949,730, issued to Pless et al on Aug. 21, 1990, all of which are incorporated herein by reference in their entireties.

The device is illustrated as being provided with six electrodes, 500, 502, 504, 506, 508 and 510. Electrodes 500 and 502 may be a pair of electrodes located in the ventricle, for example, corresponding to electrodes 124 and 126 in FIG. 2. Electrode 504 may correspond to a remote, indifferent electrode located on the housing of the implantable pacemaker/cardioverter/defibrillator.

Electrodes 506, 508 and 510 may correspond to the large surface area defibrillation electrodes located on the ventricular, coronary sinus and subcutaneous leads illustrated in FIG. 2 or to the epicardial electrodes 204,206 and 208 of FIG. 3.

Electrodes 500 and 502 are shown as hard-wired to the R-wave detector circuit, comprising bandpass filter circuit 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned, copending U.S. patent application Ser. No. 07/612,760, by Keimel, et al., filed Nov. 15, 1990 for an Apparatus for Monitoring Electrical Physiologic Signals, incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al on Nov. 14, 1989, both incorporated herein by reference in their entireties, may also usefully be employed to practice the present invention.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al, published in Biomedical Science Instrumentation, Vol. 4, pp 67-72, 1978, incorporated herein by reference in its entirety.

In the context of the present invention, it is preferable that the threshold level not be adjusted in response to paced R-waves, but instead should continue to approach the minimum threshold level following paced R-waves to enhance sensing of low level spontaneous R-waves associated with tachyarrhythmias. The time constant of the threshold circuit is also preferably sufficiently short so that minimum sensing threshold may be reached within 1-3 seconds following adjustment of the sensing threshold equal to 70-80% of the amplitude of a detected spontaneous R-wave. The invention may also be practiced in conjunction with more traditional R-wave sensors of the type comprising a band pass amplifier and a comparator circuit to determine when the bandpassed signal exceeds a predetermined, fixed sensing threshold.

Switch matrix 512 is used to select which of the available electrodes make up the second electrode pair for use in conjunction with the present invention. The second electrode pair may comprise electrode 502 or 500 in conjunction with electrode 504, 506, 508 or 510, or may comprise other combinations of the illustrated electrodes, including combinations of the large surface defibrillation electrodes 506, 508, 510. Selection of which two electrodes are employed as the second electrode pair in conjunction with the tachycardia/fibrillation discrimination function is controlled by the microprocessor 524 via data/address bus 540. Signals from the selected electrodes are passed through bandpass amplifier 534 and into multiplexer 532, where they are converted to multibit digital signals by A/D converter 530, for storage in random access memory 526 under control of direct memory address circuit 528. Microprocessor 524 analyzes the digitized ECG signal stored in random access memory 526 to identify the second fiducial point.

For example, as illustrated in FIG. 4, the microprocessor 524 may analyze the ECG stored in an interval extending from minus 100 milliseconds previous to the occurrence of an R-wave detect signal on line 564, until 100 milliseconds following the occurrence of the R-wave detect signal in order to identify the second fiducial point.

In the present case, the second fiducal point is the point of maximum slope. However, other fiducial points may also be employed, such as the point of maximum amplitude, the detected point of initiation of the detected depolarization signal or the detected point of termination of the depolarization signal. Alternatively, the second fiducal point may be determined in the same way as the first fiducal point and may be the point of detection of the depolarization signal as indicated by a second R-wave detector coupled to the second electrode pair.

Microprocessor 524 measures the time intervals δ separating the first and second fiducial points, and stores the measured intervals in random access memory 526. Microprocessor 524 also calculates the cumulative beat to beat variability of the values of δ over a preceding predetermined number of measured values of δ, according to either of the method disclosed above, and determines whether the cumulative variability is indicative of fibrillation or ventricular tachycardia.

The remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of bandpass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including antitachycardia pacing. The duration of the interval defined by the escape interval timer is determined by microprocessor 524, via data/address bus 540. The value of the count present in the escape interval counter when reset by sensed R-waves may be used to measure the duration of R-R intervals, to detect the presence of tachycardia and to determine whether the minimum rate criteria are met for activation of the tachycardia/defibrillation discrimination function.

Microprocessor 524 operates as an interrupt driven device, and responds to interrupts from pacer timing-/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an antitachyarrhythmia pacing regimen is desired, appropriate timing intervals for controlling generation of antitachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters to in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in copending, commonly assigned U.S. patent application Ser. No. 07/612,761, by Keimel, for an Apparatus for Detecting and Treating a Tachyarrhythmia, filed Nov. 15, 1990 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed. Similarly, known circuitry for controlling the timing and generation of antitachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multielectrode, simultaneous pulse regimen or a multielectrode sequential pulse regimen. Monophasic or biphasic pulses may be generated. One example of circuitry which may be used to perform this function is set forth in commonly assigned copending patent application Ser. No. 07/612,758, filed by Keimel, for an Apparatus for Delivering Single and Multiple Cardioversion and Defibrillation Pulses, filed Nov. 14, 1990, incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

As discussed above, switch matrix 512 selects which of the various electrodes are coupled to band pass amplifier 34. Amplifier 34 may be a broad band pass amplifier, having a band pass extending for approximately 0.5 to 200 hertz. The filtered EGM signal from amplifier 534 is passed through multiplexer 532, and digitized in A-D converter circuitry 530. The digitized EKG data is stored in random access memory 526 under control of direct memory address circuitry 528. Preferably, a portion of random access memory 526 is configured as a looping or buffer memory which stores at least the preceding several seconds of the ECG signal.

The occurrence of an R-wave detect signal on line 564 is communicated to microprocessor 524 via data-/address bus 540, and microprocessor 524 notes the time of its occurrence. If the tachycardia/fibrillation discrimination function is activated, microprocessor 524 waits 100 milliseconds following the occurrence of the R-wave detect signal, and thereafter transfers the most recent 200 milliseconds of digitized EGM stored in the looping or buffer memory portion of the random access memory circuit 526 to a second memory location, where the contents may be digitally analyzed to determine the point of maximum slope or other fiducial point. The transferred 200 milliseconds of stored ECG corresponds to a time window extending 100 milliseconds on either side of the R-wave detect signal. For purposes of the present invention, a sampling rate of 256 Hz should be sufficient, although somewhat lower or substantially higher sampling rates may be used, depending on the amount of data storage capacity in RAM 526 and on the processing speed of microprocessor 524.

In order to determine the point of maximum slope, the microprocessor may employ any of a number of known signal analysis techniques, such as those disclosed in U.S. Pat. No. 4,505,276 issued to Markowitz et al on Mar. 19, 1985, incorporated herein by reference in its entirety. Alternatively, Microprocessor 524 may simply compare each stored sample of the detected R-wave with the preceding sample or with several preceding samples to determine the point of maximum slope. A minimum signal threshold for detection of a point of maximum slope may also be provided as a prerequisite to identification of a point of maximum slope in order to prevent inappropriate detection due to noise signals.

In the event that no point of maximum slope is identified within the 200 milliseconds of stored ECG, random access memory 524 optionally may enter an arbitrary value. For example plus or minus 50 to 100 milliseconds from the R-wave detect signal may be entered as the second fiducal point, with the value alternating between positive and negative with each successive failure to detect a point of maximum slope. The failure to detect a point of maximum slope is most likely to arise during fibrillation, and the repeated recording of such alternate positive and negative values for $\delta$ will essentially assure that the cumulative variability measured by the tachycardia/fibrillation discriminator will result in a detection of fibrillation, as is appropriate.

Assuming that a point of maximum slope can be identified, the time interval separating this second fiducial point from the R-wave detect signal associated therewith is stored as the value of $\delta$ for that depolarization wavefront. If the second fiducial point occurs prior to the R-wave detect signal, the value of $\delta$ is negative. If the second fiducial point occurs after the R-wave detection, $\delta$ has a positive value. In this fashion, the discriminator is also sensitive to changes in directionality of propagation of the wavefront which do not greatly affect the absolute time interval separating the first and second fiducial points (e.g., a 180 degree reversal of the direction).

After the desired number of values for $\delta$ are recorded, and in response to the detection of a heart rate of sufficient rapidity to indicate the occurrence of either ventricular tachycardia or fibrillation, the microprocessor calculates the cumulative variability in the values for $\delta$, according to either method described above. The calculated cumulative variability is compared to a predetermined threshold value to distinguish tachycardia from fibrillation.

In some embodiments of the invention, it may also be desirable to vary the value of the cumulative variability threshold as a function of the average value of the preceding series of R-R intervals. For example, in the event that the preceding series of R-waves have an average rate of 200 beats per minute, a cumulative variability threshold of 100 milliseconds (T>100 ms) using the summation method or of 3 values of $V_i$ greater than 30 ms (C>2) using the rank ordered difference method, may be appropriate. However, in the presence of an average rate of 250 beats per minute, a cumulative variability threshold of 50 milliseconds using the summation method or C>2 using the rank ordered difference method may be appropriate, to reflect the increased likelihood that such extremely rapid rates are indicative of fibrillation. Using the rank ordered difference method, it may also in some cases desirable to decrease the value of "t" to which $V_i$ is compared as the detected heart rate increases or to vary the number M of values of $\delta$ employed to calculate $V_i$.

Similarly, in some embodiments of the invention it may be desirable to define an upper rate for the operation of the tachycardia/fibrillation discriminator, such that heart rates in excess of that upper rate, will always be detected as fibrillation, regardless of the variability of the stored values of $\delta$. This could also be accomplished by means of an adjustable cumulative variability threshold, gradually reduced from a maximum cumulative variability threshold. For example, using the summation method, a 100 millisecond cumulative variability threshold at the minimum rate required for activation of the discriminator function may gradually decrease to zero as the average sensed rate heart rate increases.

Figure 8:
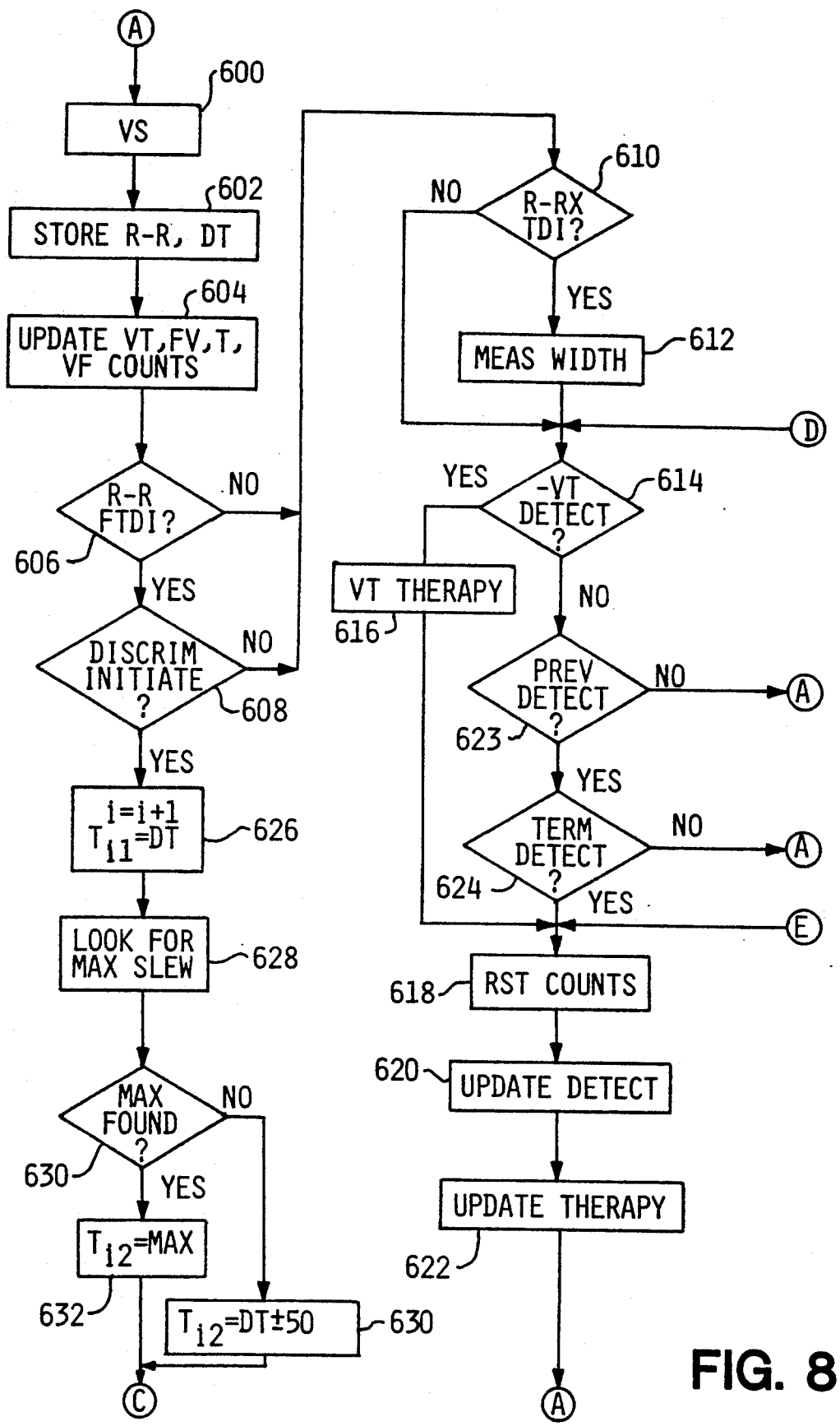
FIGS. 8 and 9 are a functional flow chart illustrating the method of discrimination between ventricular tachycardia and ventricular fibrillation provided by the present invention, and illustrating the operation of the tachycardia/fibrillation discriminator of the present invention as embodied in a microprocessor based device as illustrated in FIG. 7.
Figure 9:
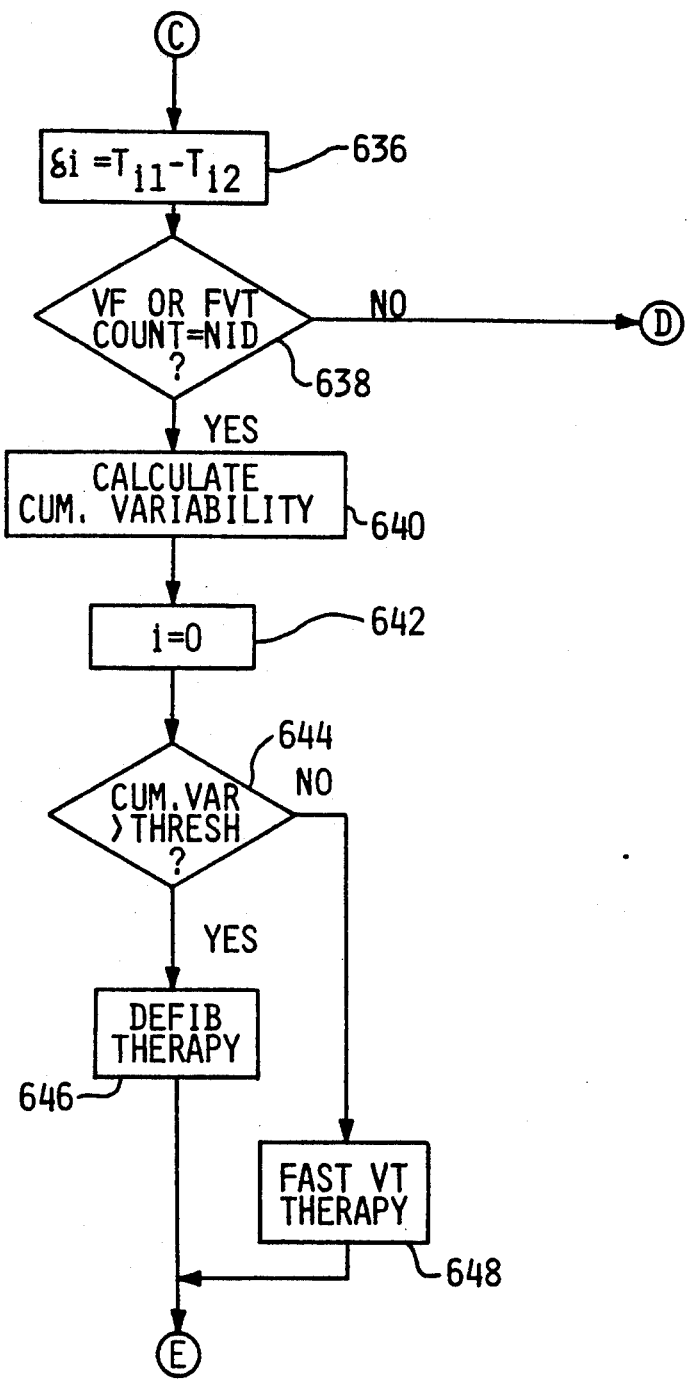

FIGS. 8 and 9 are flow charts representing the operation of the device illustrated in FIG. 7, in conjunction with the tachycardia/fibrillation discrimination function. FIGS. 8 and 9 are intended to functionally represent that portion of the software employed by microprocessor 524 (FIG. 7) which implements the tachycardia/fibrillation discrimination function. This portion of the software is executed in response to an interrupt indicating the sensing of a ventricular depolarization at 600. In response to this interrupt, the value of the preceding R-R interval, corresponding to the current time on the escape interval counter in pacer timing/control circuitry 520 may be stored at 602 and used as a measurement of the R-R interval for tachyarrhythmia detection functions. In addition, the time of detection (DT) of the sensed ventricular depolarization, as indicated by means of a real time clock within microprocessor 524 is also stored at 602 and serves as the first fiducal point associated with the detected depolarization.

At 604, the microprocessor updates counters which hold information regarding the R-R intervals previously sensed. The counters are incremented on the occurrence of a measured R-R interval falling within an associated rate range. These rate ranges may be defined by the programming stored in the RAM 526.

The first range defines a minimum R-R interval used for fibrillation detection, referred to as "FDI". The associated VF count may reflect the number of preceding sequential R-R intervals which are less than FDI, but preferably indicates how many of a first predetermined number of the preceding R-R intervals were less than FDI.

The second rate range includes R-R intervals less than a fast tachycardia interval "FTDI", and the associated FVT count may indicate either the number of preceding sequential R-R intervals which are less than FTDI and greater than FDI or may indicate how many of a second predetermined number of preceding R-R intervals were less than TDIF and greater than FDI.

The third rate range includes R-R intervals less than a lower tachycardia interval "TDI", and the associated VT count may indicate either the number of preceding sequential R-R intervals which are less than TDI and greater than FTDI or how many of a third predetermined number of preceding R-R intervals were less than TDI and greater than FTDI.

Alternatively, there may be some overlap of the rate zones, such that an R-R interval falling within the overlap zone is counted toward both the FVT and VF counts, or an R-R interval may be counted in all rate zones having defined maximum intervals greater than the measured R-R interval.

These counts, along with other stored information reflective of the previous series of R-R intervals such as information regarding the rapidity of onset of the detected short R-R intervals, the stability of the detected R-R intervals, the duration of continued detection of short R-R intervals, the average R-R interval duration and information derived from analysis of stored ECG segments are used to determine whether tachyarrhythmias are present and to distinguish between different types of tachyarrhythmias. Such detection algorithms for recognizing tachycardias are described in the above cited U.S. Pat. No. 4,726,380, issued to Vollmann, U.S. Pat. No. 4,880,005, issued to Pless et al and U.S. Pat. No. 4,830,006, issued to Haluska et al, incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7-10, 1986, IEEE Computer Society Press, pages 167-170, also incorporated by reference in its entirety herein. However, other criteria may also be measured and employed in conjunction with the present invention.

For purposes of the present example, the counts may be used to signal detection of an associated arrhythmia (ventricular fibrillation, fast ventricular tachycardia or lower rate ventricular tachycardia) when they individually reach a predetermined value, referred to herein as "NID's" (number of intervals required for detection). Each rate zone may have its own defined NID. Alternatively, detection of an arrhythmia may be based on the sum of the counts of one or more of the counts reaching a predetermined value (NID) and the particular rate range assigned to the detected arrhythmia may depend upon the relative values of the various counts (e.g. FVT and VF counts) attributable to the most recent series of R-R intervals counted toward the NID.

For purposes of the present invention, the particular details of implementation of the rate /R-R interval based VF/VT detection methodologies are not of primary importance. However, it is required the VF/VT rate detection methodologies employed by the device allow identification and detection of rhythms in the rate range in which distinction between ventricular tachycardia and ventricular fibrillation has traditionally been difficult, i.e. rates in excess of 200 beats per minute. It is also important that the discriminator function be initiated far enough in advance of the point at which a tachycardia can be detected to allow for prior measurement of the required number of values of $\delta$.

If the summation method is used, the discrimination function should be initiated and measurement of the values of $\delta$ begun on or before the time at which either the VF count or the FVT count equals its respective NID, minus "n", where "n" is the number of measured values of $\delta$ employed to calculate cumulative variability. If the ranked ordered difference method is used, the measurement of the values of $\delta$ should be initiated on or before the time at which either the VF or FVT count equals its respective NID, minus (L+M), where "L" is the number of measurements of $V_i$ employed to calculate cumulative variability and "M" is the number of previously stored values of $\delta$ compared to the current value of $\delta$ to determine the value of $V_i$. In either case, the same result could also be accomplished by initiating the measurement of $\delta$ in response to the VF count, the FVT count or the sum of the VF and FVT counts reaching a predetermined value substantially less than their respective NID's.

At 604, the VT, FVT and VF counts are updated as appropriate in response to the measured R-R interval. At 606, the preceding R-R interval is checked to determine whether it falls within either the fibrillation or fast ventricular tachycardia rate classes. If the R-R interval falls into one of these classes, The discrimination function may be initiated. Otherwise, the heart rhythm will be analyzed to determine whether the detection criteria for a lower rate tachycardia have been met at 610.

At 608, the VF and VFT counts are analyzed to determine whether the preceding series of R-R intervals meets the criterion for initiation of the VT/VF discrimination function. If the VF count and/or the FVT count meet the discriminator initiation criterion at 608, the microprocessor initiates the measurement and collection of the intervals $\delta$ separating the first and second fiducial points. If not, the microprocessor 524 checks whether the measured R-R interval is less than TDI at 610. If the R-R interval is less than TDI, the 200 ms of stored EGM associated with the most recent R-wave detect may be analyzed at 612 for waveform characteristics indicative of ventricular tachycardia. For example, the width of the QRS complex may be measured, the area under the QRS complex may be measured, or other known types of waveform analysis may be undertaken.

The microprocessor then checks to determine whether the criteria for detection of a lower rate tachycardia have been met at 614. For example, on the VT count reaching its predetermined NID value and/or the analyzed stored ECG segments meeting predetermined requirements, tachycardia may be detected. Detection of low rate tachycardia, illustrated functionally at 614, may correspond to any tachycardia detection algorithm known to the art. For example, presence of tachycardia may be confirmed by means of a measurement of average rate, sustained rate, rapid onset, rate stability, or a number of other factors known to the art as discussed in the above cited patents issued to Pless et al and Haluska et al and in the Olson et al article. However, one of the advantages of the present invention is that it is believed practicable in conjunction with virtually any prior art tachycardia detection algorithm.

If tachycardia is recognized at 614, the microprocessor 526 initiates the scheduled ventricular tachycardia treatment regimen at 616. In modern implantable pacemaker/cardioverter/defibrillators, the particular therapies are programmed into the device ahead of time by the physician, and a menu of therapies is typically provided. For example, on initial detection of tachycardia, an antitachy pacing therapy may be selected. On redetection of tachycardia, a more aggressive antitachycardia pacing therapy may be scheduled. If repeated attempts at antitachycardia pacing therapies fail, a higher level cardioversion pulse therapy may be selected thereafter. Prior art patents illustrating such preset therapy menus of antitachyarrhythmia therapies include the above-cited U.S. Pat. No. 4,830,006, issued to Haluska, et al, U.S. Pat. No. 4,727,380, issued to Vollmann et al and U.S. Pat. No. 4,587,970, issued to Holley et al. The present invention is believed practicable in conjunction with any of the known antitachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

After delivery of a tachycardia therapy at 616, the counters are reset at 618. At 620, the microprocessor updates the tachyarrhythmia detection methodologies. As discussed in the above-cited patents, in some cases it is desirable to have a different standard for redetection of a tachyarrhythmia than for initial detection of the tachyarrhythmia. Typically the criteria for redetection will be less stringent than for initial detection. Similarly, at 622, the microprocessor updates the therapy schedule, to reflect that the previously scheduled therapy had been delivered. As discussed above, in current implantable pacemaker/cardioverter/defibrillators, this generally results in the delivery of a more aggressive therapy upon redetection of tachycardia. After updating the tachyarrhythmia related functions, the microprocessor returns the device to VVI mode bradycardia pacing and awaits the next interrupt at 600.

In the event that ventricular tachycardia is not detected at 614, the microprocessor checks at 623 to determine if a tachyarrhythmia was previously detected and is not indicated to have been terminated. If no unterminated tachyarrhythmias are indicated, the microprocessor returns the device to the bradycardia pacing. If a tachyarrhythmia was detected previously, the microprocessor checks at 624 to determine whether the preceding series of R-R intervals, including the most recent, indicates a return to sinus rhythm or termination of a previously detected arrhythmia. The criterion of detection of return to sinus rhythm may be a series of a predetermined number of sequential R-R intervals which are greater than TDI, for example. Tachycardia termination criteria as set forth in the above cited Pless et al, Haluska et al or other prior art termination detection criteria may also be used. Following termination detection, the counters, detection methodologies and therapy schedules are all appropriately updated at 618, 620 and 622 and the device returns to VVI mode pacing, as discussed above.

In the event that the discriminator activation criterion is met at 608, the microprocessor begins measuring and collecting the values of $\delta$. At 626, the value, "i" indicative of the number of the present measurement of $\delta$ is incremented, and the time of occurrence of the sensed contraction or ventricular pacing pulse at 600 (DT) is entered as $T_{i1}$. One hundred milliseconds following the detection of a ventricular depolarization at 600, the portion of the random access memory serving as the EGM buffer is frozen, and the most recent 200 milliseconds of digitized EGM signal is transferred to a separate memory location within the random access memory for analysis. Under control of microprocessor 524, the point of maximum slope is identified at 628. Using the digital data processing techniques discussed above, the point of maximum slew may be identified as either the point of greatest slope, positive or negative, or may be identified as the point of greatest positive slope or the point of greatest negative slope, as may be desired. If a point of maximum slew is identified as indicated at 630, the time of maximum slew is set equal to $T_{i2}$ at 632. If no maximum slew point is found, an arbitrary value, for example plus or minus 50 milliseconds as discussed above may be recorded for the value of $T_{i2}$, at 630. Assuming that values of $T_{i1}$ and $T_{i2}$ have successfully been entered, $\delta_i$ is calculated at 636, and stored.

While the embodiment discussed in conjunction with FIGS. 7-9 alternately measures the maximum slope and the width of a detected signal indicative of a depolarization, both forms of analysis could be performed with all detected depolarizations associated with R-R intervals indicative of any tachyarrhythmia, if sufficient computational speed is available. However, the alternate use of width and slope analysis for low rate tachycardia and VT/VF discrimination, respectively, is believed to provide a workable approach in devices having computational and memory capabilities in line with the current and probable next generation of implantable pacemaker/cardioverter/defibrillators.

At 638, the microprocessor checks to determine whether the VF count or the FVT count is greater than or equal to their corresponding NID's, indicating detection of high rate ventricular tachycardia or fibrillation. As discussed above, an alternative criterion for detection of ventricular fibrillation of fast ventricular tachycardia may employ the sum of the VF and FVT counts. If ventricular fibrillation or fast ventricular tachycardia is not detected, the microprocessor returns to the lower rate tachycardia detection function at 614.

In the event that fast ventricular tachycardia or ventricular fibrillation detection criteria are met at 638, the discriminator calculation is performed at 640, measuring the cumulative variability over the preceding series of R-R intervals using one of the two methods discussed above. The value of i is reset to zero at 642. At 644, the calculated cumulative variability is compared with the cumulative variability threshold using one of the methods discussed above. If the cumulative variability is greater than or equal to the threshold, fibrillation therapy is selected at 646. If the cumulative variability is less than the threshold, fast ventricular tachycardia therapy is selected at 648.

Therapies for fast ventricular tachycardia may be of the same general types provided in conjunction with detection of ventricular tachycardia at 616 (FIG. 8), and may include antitachycardia pacing and cardioversion pulse therapies. However, the therapy menu for fast ventricular tachycardia will be more aggressive than the therapy set for slower ventricular tachycardias. For example, fewer or no attempts at antitachy pacing may be undertaken prior to delivery of cardioversion pulses. Higher amplitude cardioversion pulses may be specified.

The references cited above in conjunction with descriptions of prior art tachycardia detection and treatment therapies are applicable here as well. Again, the focus of the present invention is to distinguish fibrillation from tachycardias. It is believed that in the context of practicable devices, the physician will be provided with the ability to select which of a number of available therapies are provided in response to the detection of slow or fast tachycardias.

In the event that fibrillation is identified at 646, the typical therapy will be delivery of a high amplitude defibrillation pulse, typically in excess of 10 joules, and in some cases as much as 35 joules or more. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation.

Following delivery of the defibrillation pulse or tachycardia therapy, the tachyarrhythmia functions are updated at 618, 620 and 622 to reflect the delivery of the selected therapy. The microprocessor then returns to the device to VVI pacing and, and awaits the next successive interrupt due to ventricular pacing or the occurrence of a sensed ventricular depolarization at 600.

Figure 10:
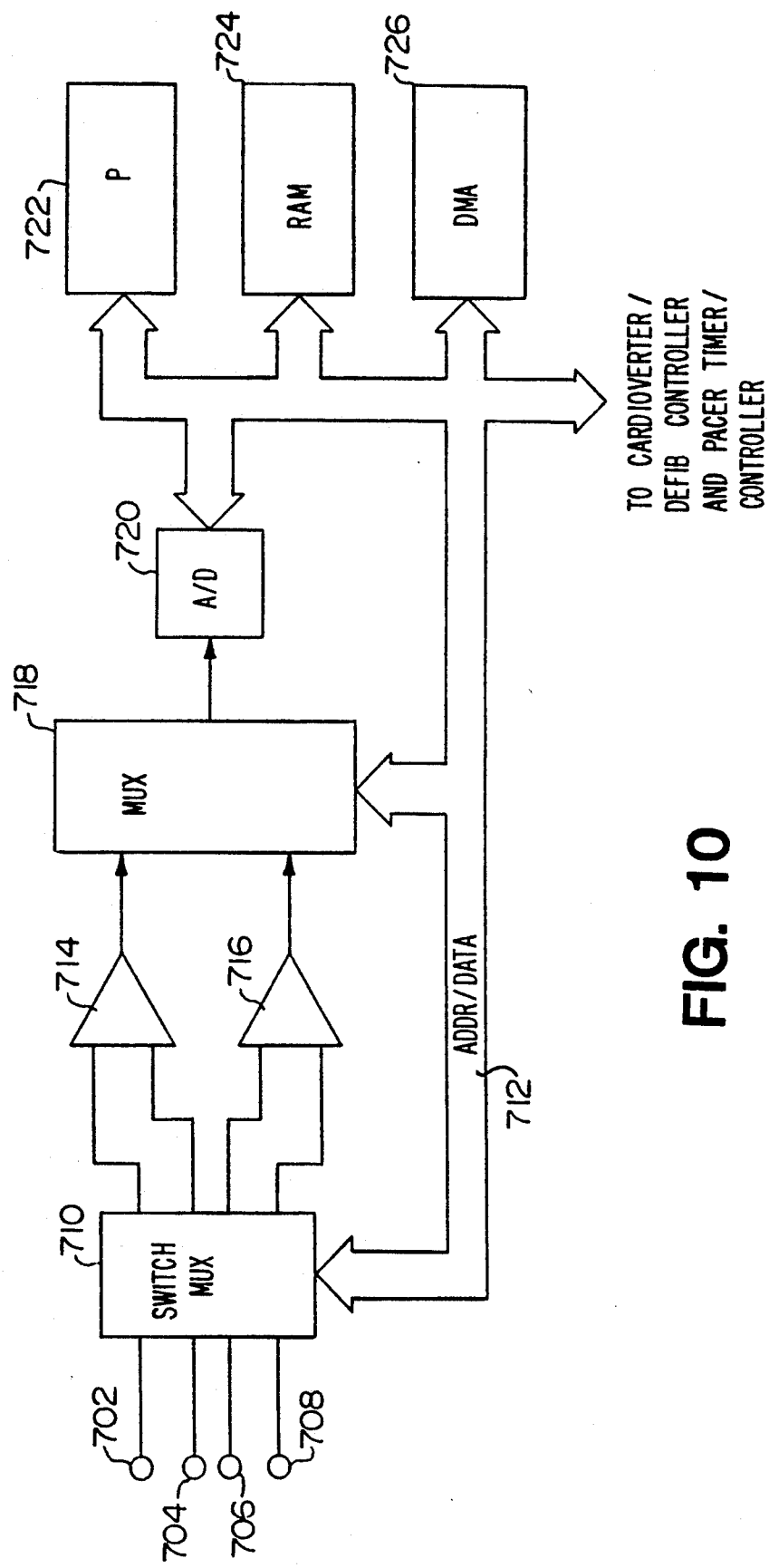
FIG. 10 is a block schematic diagram illustrating an alternative embodiment of an implantable pacemaker/cardioverter/defibrillator in which the present invention may be embodied, illustrating a modification to the circuitry of FIG. 7.

FIG. 10 is a block diagram of an alternative embodiment of the present invention, substituting somewhat different circuitry for the portion of the circuitry illustrated in FIG. 7 which performs the tachycardia/fibrillation discrimination function. In the apparatus illustrated in this figure, both fiducial points are determined by means of digital signal processing. A switch matrix 710 is provided which selects which of four electrodes 702, 704, 706 and 708 are coupled to band pass amplifiers 714 and 716. Band pass amplifiers 714 and 716 may have the same band pass characteristics, or may have differing band pass characteristics if desired. The signals from band pass amplifiers 714 and 716 are provided to digital multiplexer 718, which alternately samples the signal from band pass amplifiers 714 and 716 and applies it to A/D converter 720. The output of A/D converter 720 is stored in random access memory 724 under control of direct memory address circuitry 726. Preferably, portions of random access memory 724 are configured as data buffers, each capable of storing the preceding several seconds of digitized EGM signals. The stored EGM signals are analyzed by microprocessor 722 to detect the relative times of occurrence of first and second defined fiducial points, recording the difference in their occurrence times ($\delta$), and performing the tachycardia/fibrillation detection discrimination function as discussed above. The defined fiducial points may be the same, or may be different, with regard to the stored digitized ECG signals from buffer amplifiers 714 and 716. Similarly, the electrodes coupled between amplifiers 714 and 716 by switch matrix 710 may be two separate sets of electrodes, two sets of electrodes with one electrode in common, or may in some cases, employ the same set of electrodes, provided that the selected fiducial points are different from one another. Selected fiducial points may include, for example, the identified beginning or end of sensed R waves, the point of maximum amplitude of sensed R waves, the point of maximum slope of sensed R waves, or may be based on other identifiable characteristics of the recorded EGM signals.

Figure 11:
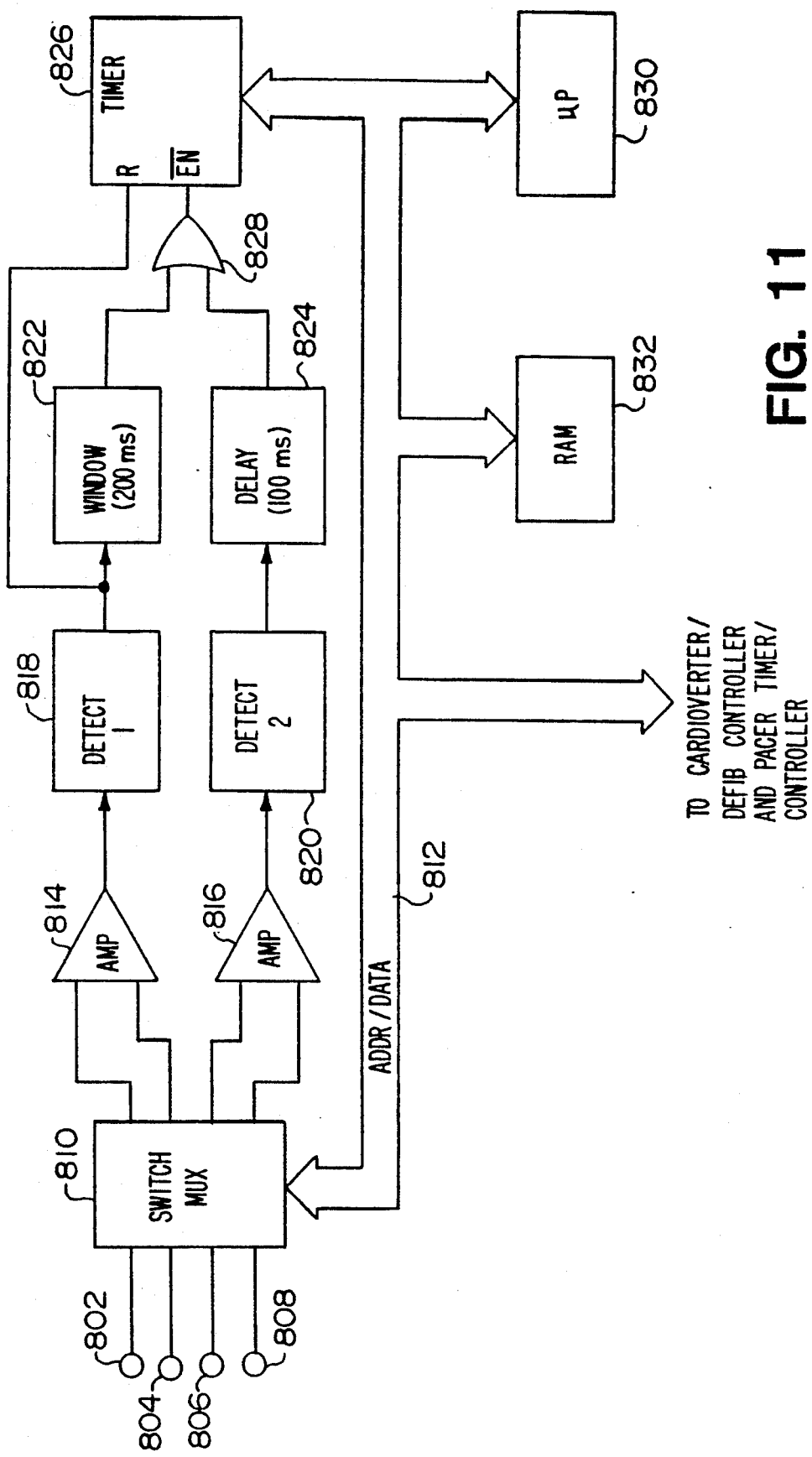
FIG. 11 illustrates an additional alternative embodiment of a pacemaker/cardioverter/defibrillator in which the present invention may be practiced, and also illustrates a modification to the circuitry of FIG. 7.

FIG. 11 shows a second alternative embodiment, in which dedicated circuitry is employed to perform the fiducial point detection and the measurement of the time intervals $\delta$ separating the first and second fiducial points. Similar to the apparatus illustrated in FIG. 10, the apparatus of FIG. 11 is provided with a set of electrodes 802, 804, 806 and 808 which are applied to amplifiers 816 and 814 by switch matrix 810. Included in this embodiment of the invention are separate, dedicated fiducial point detection circuitry blocks 818 and 820. One detection block, for example block 818, may correspond to an R wave detector as discussed in conjunction with FIG. 7. The second detector 820 may, for example, be an analog circuit capable of detecting the point of maximum amplitude of the sensed R wave, or may include a differentiation circuit coupled to a peak detector for detecting the maximum slope of the sensed R wave. In any case, circuits 818 and 820 provide output pulses upon occurrence of their respectively detected fiducial points. The output pulse from circuitry 818 initiates a time window of 200 milliseconds determined by timer 822. The signal from detection circuitry 820 is delayed by 100 milliseconds by timer 824.

On generation of the detection signal from circuitry 818, timer 826 is reset, and begins timing. Following the earliest of the time out of timer 822 or timer 824, the clock signal to timer 826 is disabled via OR gate 828. The value stored in timer 826, at this point, will reflect the timing difference between the detection of the two fiducial points.

The combination of timers 822, 824 and 826 produce a system in which, if both fiducial points occur at the same time, the timer 826 will hold a count corresponding to 100 milliseconds. Thus, phase information in the form of the order of occurrence of the two fiducial points is preserved, and can be recovered by the microprocessor by subtracting a value equivalent to 100 milliseconds from the stored time interval in timer 826, to provide either a positive or a negative value of $\delta$. Microprocessor 830 and random access memory 832 correspond to those illustrated in FIG. 7, are interconnected with the remainder of the cardioversion, defibrillation and pacing circuitry in a manner analogous to that illustrated in FIG. 7. Alternatively, microprocessor 830 could be replaced by full custom digital circuitry or even analog circuitry dedicated specifically to performance of the discriminator function.

Figure 12:
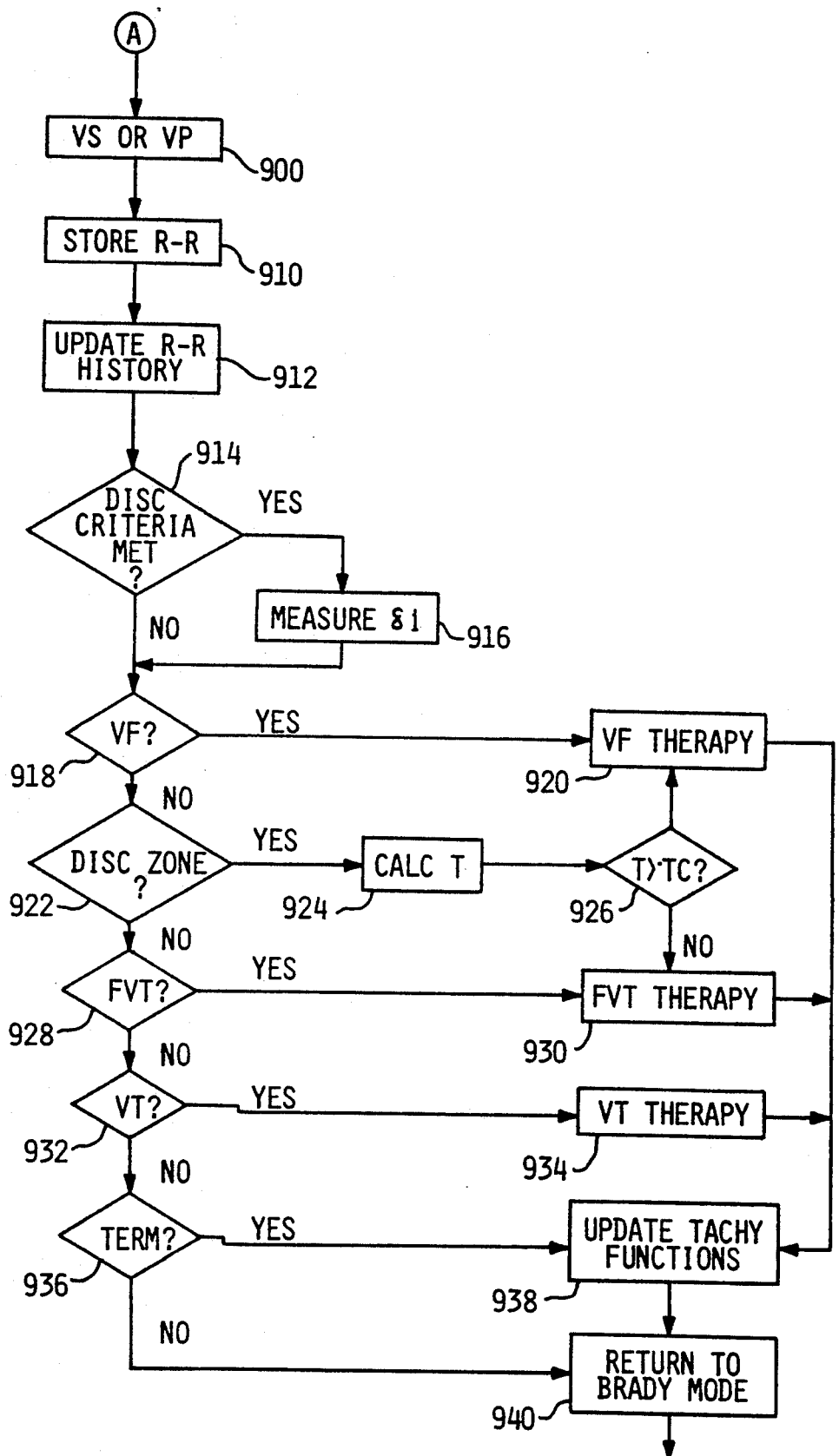
FIG. 12 is a functional flow chart illustrating an alternative method of discrimination between ventricular tachycardia and ventricular fibrillation provided by the present invention, and illustrating the operation of the tachycardia/fibrillation discriminator of the present invention as embodied in a microprocessor based device.

FIG. 12 is a generic functional flow chart intended to illustrate the basic mechanism by which the VF/VT discrimination function of the present invention may be added to or employed with a prior art implantable pacemaker/cardioverter/defibrillator of the type which provide differing levels of therapy depending the diagnosed tachyarrhythmia. The flow chart of FIG. 12 is purely a functional flow chart, and may reflect the operation of a microprocessor device or may equally well reflect the operation of a device fabricated employing full custom digital circuitry, or even analog circuitry.

At 900, it is assumed that a ventricular depolarization is sensed or a ventricular pacing pulse is delivered, while the device is operating in VVI bradycardia pacing mode. The R-R interval ending with the sensed depolarization or the delivered pacing pulse is stored and measured at 910, and the history of recent stored R-R intervals is updated at 812 to reflect the most recently measured R-R interval.

At 914, the device reviews the R-R interval history to determine whether criteria for activating the VT/VF discriminator are met. As discussed above, this is preferably a sequence of R-R intervals indicating a high likelihood a cardiac rhythm which could be diagnosed as either ventricular fibrillation or fast ventricular tachycardia is underway. In the event that the discriminator criteria are met at 914, the value of $\delta_i$ is measured at 916, and the device steps through its hierarchy of detection criteria.

As illustrated, the device is provided with five detection criteria including ventricular fibrillation detection criteria at 918, VT/VF discriminator zone criteria at 922, fast ventricular tachycardia criteria at 928, ventricular tachycardia criteria at 932 and arrhythmia termination or sinus rhythm detection criteria at 936. The device attempts to classify the current cardiac rhythm into one of these five categories, based on the R-R interval history. As illustrated, separate VF zone, discrimination zone and FVT zone criteria are envisioned. However, as disclosed in conjunction with the flow charts in FIGS. 8 and 9, these three classifications may all be reduced to a single classification, if the operative zone of operation of the VT/VF discriminator is extended to include any cardiac rhythm meeting either VF or FVT detection criteria.

At 918, the R-R interval history is checked to determine whether it unambiguously identifies the occurrence of ventricular fibrillation. For example, a rate in excess of 250-280 beats per minute may be used to unambiguously identify ventricular fibrillation. In the event that ventricular is identified, ventricular fibrillation therapy, typically a single high energy pulse is delivered at 920.

In the event that a rhythm which might be diagnosed as either ventricular fibrillation or fast ventricular tachycardia is detected at 922, the cumulative variability of the measured values of δ is calculated, and the cumulative variability is compared to a threshold value at 926. For example, R-R intervals indicative of a cardiac rhythm of greater than 180-200 beats per minute, but less than 250-280 beats per minute might define the rate discriminator operation zone specified at 922. In the event that the cumulative variability is less than the threshold cumulative variability, a fast tachycardia therapy, such as cardioversion pulses or antitachycardia pacing is delivered at 930. In the event that the cumulative variability is greater than the threshold variability at 926, ventricular fibrillation therapy is delivered at 920.

In the event that fast ventricular tachycardia is unambiguously identified at 928, fast ventricular tachycardia therapy is delivered at 930. For example, fast ventricular tachycardia may be identified in response to heart rhythms having a rate between 180 and 200 beats per minute. As discussed above, an alternative is to define a VF/VT discriminator rate zone which extends through and includes both the fast ventricular tachycardia and ventricular fibrillation rate zones, allowing for omission of the functional blocks illustrated at 918 and 928.

In the event that the rhythm is diagnosed as a slower tachycardia at 932, a less aggressive ventricular tachycardia therapy is delivered at 934, for example, a series of attempts at antitachycardia pacing may be prescribed. In the event that tachycardia is not detected, the device checks at 936 to determine whether a tachyarrhythmia had previously been detected and whether the tachyarrhythmia has been terminated, i.e., whether the patient has returned to a normal sinus rhythm. For example, a sequence of several R-R intervals at less than the rate required to detect ventricular tachycardia may be used to detect termination. Tachycardia detection and treatment functions such as the R-R interval history, the detection criteria for the various rate zones and the therapy menus may be updated at 938, and the device returns to bradycardia pacing mode at 940, to await the next sensed ventricular contraction or ventricular pacing pulse at 900. Similarly, after delivery of any of the various antitachycardia or defibrillation therapies, the tachyarrhythmia detection and therapy menus are updated at 938 to reflect the tachyarrhythmias detected and the therapies delivered, and the device returns to bradycardia pacing at 940. In the event that none of the detection criteria are met, as indicated by a failure to detect sinus rhythm or termination of tachyarrhythmia at 936, the device simply returns to the brady pacing mode, and awaits the next subsequent sensed ventricular contraction or ventricular pacing pulse at 900.

FIGS. 10 and 11 are included to illustrate the scope of applicability of the present invention, and that it can be practiced in conjunction with implantable pacemaker/cardioverter/defibrillators in which signal processing is done in an essentially analog fashion, in essentially digital fashion, or any mix thereof. FIGS. 10 and 11 are also intended to indicate that the scope of the invention should not be construed as limited by the functional schematic of FIG. 7, which, like FIGS. 10 and 11 should be considered illustrative, rather than limiting with regard to the scope of the claims that follow.

FIG. 12 is intended to illustrate the broad applicability of the VT/VF discriminator provided by the present invention, and provide general guidance as to incorporation of the invention into pacemaker/cardioverter/defibrillators of any of the known types and in future such devices. The broad applicability of the discriminator in the present application is believed to be one of its most valuable attributes.

Furthermore, it should be recognized that although the disclosed embodiment deals with fibrillation and tachycardia in the lower chambers or ventricles of the heart, the invention may be usefully practiced in the context of the upper chambers or atria of the heart, which are also prone to tachycardia and fibrillation in some patients. In addition, while the therapies discussed in conjunction with the disclosed embodiment generally relate to delivery of electrical pulses, it should be understood that the invention may be usefully practiced in conjunction with any device adapted to deliver differing therapies for tachycardia and fibrillation, including drug therapies, non-pulsatile electrical therapies, and any other such therapies as may be implemented in such devices as their development progresses, whether applied directly to the heart or systemically.

Similarly, it should be understood that the discriminator of the present invention, while particularly adapted for use in or in conjunction with an implantable cardioverter/defibrillator may also in some cases be usefully practiced in conjunction with a non-implantable device, in a device which, for example only treats fibrillation or only treats tachycardia, or even in a device adapted primarily for diagnostic purposes.

In conjunction with above application, we claim:

1. A cardioverter/defibrillator, comprising:
   treatment means for delivering a first therapy to a patient's heart to treat tachycardia and a second therapy to said patient's heart to treat fibrillation;
   first means for sensing electrical signals from said patient's heart indicative of the depolarization of said patient's heart;
   second means for sensing electrical signals from said patient's heart indicative of the depolarization of said patient's heart;
   means for defining a first criterion indicative of a depolarization of said patient's heart;
   means for defining a second criterion indicative of a depolarization of said patient's heart;
   first fiducial point detection means, coupled to said first sensing means for determining the time at which the electrical signal sensed by said first sensing means meets said first criterion and for issuing a first fiducial point signal indicative thereof;
   second fiducial point detection means, coupled to said second sensing means for determining the time at which the electrical signal sensed by said second sensing means meets said second criterion and for issuing a second fiducial point signal indicative thereof; and
   tachycardia/fibrillation discriminator means responsive to said first and second fiducial point signals comprising means for defining time intervals based on the times of occurrence of said first fiducal point signals, means for detecting failures of said second fiducal point signals to occur within said defined time intervals, and means responsive to said detected failures for selecting between said first and second therapies.

2. A cardioverter/defibrillator, comprising:
treatment means for delivering a first therapy to a patient's heart to treat tachycardia and a second therapy to said patient's heart to treat fibrillation;
first means for sensing electrical signals from said patient's heart indicative of the depolarization of said patient's heart and for issuing a first fiducial point signal indicative of a depolarization of said patient's heart, said first sensing means comprising a first electrode pair;
second means for sensing electrical signals from said patient's heart indicative of the depolarization of said patient's heart and for issuing a second fiducial point signal indicative of a depolarization of said patient's heart, said second sensing means comprising a second electrode pair including at least one electrode not included in said first electrode pair;
tachycardia/fibrillation discriminator means responsive to said first and second fiducal point signals for cumulatively measuring the variability of the depolarization wavefront within said patient's heart over a series of depolarizations of said patient's heart and means for selecting between said first and second therapies as a function of said measured variability, said discriminator means comprising means for defining time intervals based on the times of occurrence of said first fiducal point signals, means for detecting failures of said second fiducal point signals to occur within said defined time intervals, and means responsive to said detected failures for selecting between said first and second therapies.

3. A cardioverter/defibrillator according to claim 1 or claim 2 wherein said variability measuring means comprises means responsive to said first and second fiducial point signals for measuring time intervals separating said first and second fiducal point signals.

4. A cardioverter/defibrillator according to claim 3 wherein said variability measuring means comprises means for measuring the variability of said measured time intervals over a series of depolarizations of said patient's heart.

5. A cardioverter/defibrillator according to claim 4 wherein said tachycardia/fibrillation discriminator means comprises means for defining a time value in response to a said failure of a second fiducal point signal to occur within a said defined time interval, and wherein said variability measuring means comprises means responsive to said time value for measuring said variability.

6. A defibrillator, comprising:
treatment means for delivering a defibrillation therapy to a patient's heart to treat to treat fibrillation;
first means for sensing electrical signals from said patient's heart indicative of the depolarization of said patient's heart and for providing a first fiducial point signal indicative thereof, said first sensing means comprising a first electrode pair;
second means for sensing electrical signals from said patient's heart indicative of the depolarization of said patient's heart and for providing a second fiducal point signal indicative thereof, said second sensing means comprising a second electrode pair including at least one electrode not included in said first electrode pair;
fibrillation detection means responsive to said first and second fiducal point signals for measuring the variability of wavefront propagation within said patient's heart over a series of depolarizations of said patient's heart, said variability measuring means comprising means for defining time intervals based on times of occurrence of said first fiducal point signals, means for detecting failures of said second fiducal point signals to occur within said defined time intervals, and means responsive to said detected failures for initiating said defibrillation therapy.

7. A cardioverter, comprising:
treatment means for delivering an anti-tachycardia therapy to a patient's heart to treat to treat tachycardia;
first means for sensing electrical signals from said patient's heart indicative of the depolarization of said patient's heart and for providing a first fiducial point signal indicative thereof, said first sensing means comprising a first electrode pair;
second means for sensing electrical signals from said patient's heart indicative of the depolarization of said patient's heart and for providing a second fiducal point signal indicative thereof, said second sensing means comprising a second electrode pair including at least one electrode not included in said first electrode pair;
tachycardia detection means responsive to said first and second fiducal point signals comprising means for measuring the variability of wavefront propagation within said patient's heart over a series of depolarizations of said patient's heart, said variability measuring means comprising means for defining time intervals based on times of occurrence of said first fiducal point signals, means for detecting failures of said second fiducal point signals to occur within said defined time intervals, and means responsive to said detected failures for initiating said anti-tachycardia therapy.

8. Apparatus for detecting fibrillation, comprising:
means for defining a first criterion indicative of a depolarization of said patient's heart;
means for defining a second criterion, different from said first criterion, indicative of a depolarization of said patient's heart;
first means for sensing electrical signals from said patient's heart indicative of the depolarization of said patient's heart and for providing a first fiducial point signal indicative thereof in response to said electrical signals meeting said first criterion;
second means for sensing electrical signals from said patient's heart indicative of the depolarization of said patient's heart and for providing a second fiducal point signal indicative thereof in response to said electrical signals meeting said second criterion;
fibrillation identification means responsive to said first and second fiducial point signals comprising means for defining time intervals based on times of occurrence of said first fiducal point signals, means for detecting failures of said second fiducal point signals to occur within said defined time intervals, and means responsive to said detected failures for identifying the occurrence of fibrillation.

* * * * *